US011971356B2

(12) United States Patent
Attar et al.

(10) Patent No.: US 11,971,356 B2
(45) Date of Patent: *Apr. 30, 2024

(54) BODILY EMISSION ANALYSIS

(71) Applicant: OUTSENSE DIAGNOSTICS LTD., Or Yehuda (IL)

(72) Inventors: Ishay Attar, M.P. Hof Carmel (IL); Yaara Kapp-Barnea, Nirit (IL)

(73) Assignee: OUTSENSE DIAGNOSTICS LTD., Or Yehuda (IL)

( * ) Notice: Subject to any disclaimer, the term of this patent is extended or adjusted under 35 U.S.C. 154(b) by 0 days.

This patent is subject to a terminal disclaimer.

(21) Appl. No.: 18/085,685

(22) Filed: Dec. 21, 2022

(65) Prior Publication Data

US 2023/0121436 A1 Apr. 20, 2023

Related U.S. Application Data

(63) Continuation of application No. 17/462,147, filed on Aug. 31, 2021, now Pat. No. 11,561,181, which is a (Continued)

(51) Int. Cl.
*G01N 21/64* (2006.01)
*A61B 10/00* (2006.01)
(Continued)

(52) U.S. Cl.
CPC ..... *G01N 21/6486* (2013.01); *A61B 10/0038* (2013.01); *A61B 10/007* (2013.01); (Continued)

(58) Field of Classification Search
CPC ............. G01N 21/6486; G01N 21/645; G01N 33/493; G01N 2021/6421; A61B 10/0038; (Continued)

(56) References Cited

U.S. PATENT DOCUMENTS 4,636,474 A 1/1987 Ogura et al.
5,277,181 A 1/1994 Mendelson et al.
(Continued)

FOREIGN PATENT DOCUMENTS

EP 1167971 A2 1/2002
EP 3159691 A1 4/2017
(Continued)

OTHER PUBLICATIONS

Notice of Allowance for U.S. Appl. No. 17/412,962 dated Jun. 13, 2023.
(Continued)

*Primary Examiner* — David P Porta
*Assistant Examiner* — Meenakshi S Sahu
(74) *Attorney, Agent, or Firm* — Dorsey & Whitney LLP

(57) ABSTRACT

Apparatus and methods are described for use with feces of a subject that are disposed within a toilet bowl. One or more light sensors receive light from the toilet bowl, while the feces are disposed within the toilet bowl. A computer processor detects a set of three or more spectral components that have a characteristic relationship with each other in a light spectrum of bile, by analyzing the received light, and detects a presence of bile within the feces, in response to detecting the set of three or more spectral components. The computer processor generates an output in response thereto. Other applications are also described.

21 Claims, 14 Drawing Sheets

Related U.S. Application Data continuation of application No. 16/325,632, filed as application No. PCT/IL2017/050966 on Aug. 30, 2017, now Pat. No. 11,467,091.

(60) Provisional application No. 62/381,288, filed on Aug. 30, 2016.

(51) Int. Cl.
| | |
|---|---|
| *E03D 11/13* | (2006.01) |
| *G01J 3/10* | (2006.01) |
| *G01J 3/28* | (2006.01) |
| *G01J 3/42* | (2006.01) |
| *G01J 5/0806* | (2022.01) |
| *G01J 5/0808* | (2022.01) |
| *G01J 5/10* | (2006.01) |
| *G01N 21/31* | (2006.01) |
| *G01N 33/493* | (2006.01) |
| *G01N 33/574* | (2006.01) |

(52) U.S. Cl.
CPC .............. *G01J 3/10* (2013.01); *G01J 3/2803* (2013.01); *G01J 5/0806* (2013.01); *G01J 5/0808* (2022.01); *G01J 5/10* (2013.01); *G01N 21/31* (2013.01); *G01N 21/645* (2013.01); *G01N 33/493* (2013.01); *A61B 2010/0006* (2013.01); *E03D 11/13* (2013.01); *G01J 2003/104* (2013.01); *G01J 3/42* (2013.01); *G01N 2021/6421* (2013.01); *G01N 33/57419* (2013.01)

(58) Field of Classification Search
CPC ... A61B 10/007; A61B 2010/0006; G01J 3/42
See application file for complete search history.

(56) References Cited

U.S. PATENT DOCUMENTS

| | | | |
|---|---|---|---|
| 5,730,149 | A | 3/1998 | Nakayama et al. |
| 6,006,119 | A | 12/1999 | Soller et al. |
| 6,572,564 | B2 | 6/2003 | Ito et al. |
| 6,844,195 | B2 | 1/2005 | Craine |
| 7,749,217 | B2 | 7/2010 | Podhajsky |
| 8,750,952 | B2 | 6/2014 | Aalders |
| 8,911,368 | B2 | 12/2014 | Rabinovitz et al. |
| 9,029,161 | B2 | 5/2015 | Aalders et al. |
| 10,575,830 | B2 * | 3/2020 | Attar .................. G01J 3/42 |
| 11,129,599 | B2 * | 9/2021 | Attar .................. G06T 7/0014 |
| 11,467,091 | B2 * | 10/2022 | Attar .................. A61B 10/007 |
| 11,561,181 | B2 * | 1/2023 | Attar .................. G01J 3/10 |
| 2003/0232446 | A1 | 12/2003 | Scholl et al. |
| 2005/0037505 | A1 | 2/2005 | Samsoondar |
| 2005/0154277 | A1 | 7/2005 | Tang et al. |
| 2005/0261605 | A1 | 11/2005 | Shemer et al. |
| 2010/0099139 | A1 | 4/2010 | Ben-David et al. |
| 2011/0051125 | A1 | 3/2011 | Kim |
| 2011/0306855 | A1 | 12/2011 | Rabinovitz et al. |
| 2012/0196271 | A1 | 8/2012 | Ingber |
| 2014/0147924 | A1 | 5/2014 | Wheeldon et al. |
| 2015/0359522 | A1 | 12/2015 | Recht et al. |
| 2016/0000378 | A1 | 1/2016 | Hall et al. |
| 2016/0120449 | A1 | 5/2016 | Chiba |
| 2016/0278705 | A1 | 9/2016 | Han et al. |
| 2017/0303901 | A1 | 10/2017 | Sekine |
| 2017/0307512 | A1 | 10/2017 | Akagawa et al. |
| 2018/0085098 | A1 | 3/2018 | Attar |
| 2018/0303466 | A1 | 10/2018 | Kashyap et al. |
| 2019/0195802 | A1 | 6/2019 | Attar et al. |
| 2020/0100771 | A1 | 4/2020 | Attar |
| 2021/0389250 | A1 | 12/2021 | Attar et al. |

FOREIGN PATENT DOCUMENTS

| | | |
|---|---|---|
| JP | H05126826 A | 5/1993 |
| JP | H07113804 | 5/1995 |
| JP | H0978656 A | 3/1997 |
| JP | H1114622 A | 1/1999 |
| JP | 2000241347 A | 9/2000 |
| JP | 2005037278 A | 2/2005 |
| JP | 2005524441 A | 8/2005 |
| JP | 2006189338 A | 7/2006 |
| JP | 2007252805 A | 10/2007 |
| JP | 2012532122 A | 12/2012 |
| JP | 2015500471 A | 1/2015 |
| JP | 2016004005 A | 1/2016 |
| JP | 2020201279 A | 12/2020 |
| KR | 20170078450 A | 7/2017 |
| WO | 2011123776 A2 | 10/2011 |
| WO | 2013082267 A1 | 6/2013 |
| WO | 2014171018 A1 | 10/2014 |
| WO | 2014192781 A1 | 12/2014 |
| WO | 2015194405 A1 | 12/2015 |
| WO | 2016063547 A1 | 4/2016 |
| WO | 2016135735 A1 | 9/2016 |
| WO | 2018042431 A1 | 3/2018 |
| WO | 2018222939 A1 | 12/2018 |
| WO | 2021205345 A1 | 10/2021 |

OTHER PUBLICATIONS

Office Action for Japanese Application No. 2022-075244 dated Jul. 3, 2023.
Office Action for Japanese Application No. 2022-075244 dated Mar. 3, 2023.
Examination Report for Canadian Application No. 2,977,743 dated Dec. 16, 2022.
Issue Notification for U.S. Appl. No. 17/462,147 dated Jan. 4, 2023.
Office Action for Japanese Application No. 2022-022279 dated Feb. 3, 2023.
Imai, et al., "The Effective Method of Feces for Occult Blood Test in the Detection of Colorectal Cancer", Second Department of Surgery, Yokohama City University, School of Medicine, 1992, 9 pages.
Corrected Notice of Allowability for U.S. Appl. No. 17/462,147 dated Nov. 17, 2022.
Corrected Notice of Allowance for U.S. Appl. No. 15/553,366 dated Jan. 29, 2020.
Corrected Notice of Allowance for U.S. Appl. No. 15/553,366 dated Nov. 18, 2018.
European Search Report for European Application No. 16754866.8 dated Nov. 15, 2018.
Examination Report for Australian Application No. 2016224850 dated May 3, 2021.
Examination Report for Australian Application No. 2016224850 dated Sep. 11, 2020.
Examination Report for CA2,977,743 dated Mar. 22, 2022.
Extended European Search Report for European Patent Application No. 21180648.4 dated Oct. 28, 2021.
First Action Interview Office Action received for U.S. Appl. No. 16/700,423 dated Feb. 5, 2021.
International Search Report and Written Opinion from International Application No. PCT/IB2021/052856 dated Sep. 3, 2021.
International Search Report and Written Opinion from International Application No. PCT/IL2016/050223 dated Jun. 7, 2016.
International Search Report and Written Opinion from International Application No. PCT/IL2017/050966 dated Nov. 28, 2017.
Invitation to Pay Additional Fees for International Application No. PCT/IB2021/052856 dated Jul. 8, 2021.
Issue Notification for U.S. Appl. No. 15/553,366 dated Dec. 11, 2019.
Issue Notification for U.S. Appl. No. 16/325,632 dated Sep. 21, 2022.
Non-Final Office Action for U.S. Appl. No. 15/553,366 dated Feb. 11, 2019.

(56) References Cited

OTHER PUBLICATIONS

Non-Final Office Action for U.S. Appl. No. 17/412,962 dated Nov. 28, 2022.
Notice of Allowance for U.S. Appl. No. 17/462,147 dated Sep. 28, 2022.
Notice of Allowance for U.S. Appl. No. 15/553,366 dated Aug. 28, 2019.
Notice of Allowance for U.S. Appl. No. 16/325,632 dated Aug. 9, 2022.
Notice of Allowance for U.S. Appl. No. 16/700,423 dated May 27, 2021.
Office Action and English Summary for Chinese Application No. 201680015869.0 dated Aug. 16, 2019.
Office Action and English Translation for Japanese Application No. 2017-544028 dated Dec. 3, 2019.
Office Action for Chinese Application No. 201680015869.0 dated Jun. 5, 2020.
Office Action for Japanese Application No. 2019-510400 dated Jul. 7, 2021.
Office Action for Japanese Application No. 2020-146892 dated Sep. 15, 2021.
Office Action for KR 10-2017-7027062 dated Apr. 25, 2022 with English machine translation and partial English translation by associate.
Preinterview First Office Action for U.S. Appl. No. 16/700,423 dated Dec. 24, 2020.
Supplementary Extended European Search Report for Application No. 17845672.9 dated Jul. 17, 2019.
U.S. Appl. No. 15/553,366, filed Aug. 24, 2017.
U.S. Appl. No. 16/325,632, filed Feb. 14, 2019.
U.S. Appl. No. 16/700,423, filed Dec. 2, 2019.
U.S. Appl. No. 17/412,962, filed Aug. 26, 2021.
U.S. Appl. No. 17/462,147, filed Aug. 31, 2021.
U.S. Appl. No. 62/120,639, filed Feb. 25, 2015.
U.S. Appl. No. 62/381,288, filed Aug. 30, 2016.
Cullen, et al., "Hyperspectral Imaging for Non-Contact Analysis of Forensic Traces", Forensic Science International, Oct. 22, 2012.
Monici, "Natural flourescence of white blood cells: spectroscopic and imaging study", Journal of Photochemistry and photobilology B:Biology 30, 1995, pp. 29-37.
Russo, et al., "Hemoglobin, Isolation and Chemical Properties", Journal of Chemical Education, May 1973, pp. 347-350.
Corrected Notice of Allowance for U.S. Appl. No. 17/412,962 mailed Sep. 19, 2023.
Issue Notification for U.S. Appl. No. 17/412,962 mailed Sep. 27, 2023.
Office Action for Japanese Application No. 2022-022279 mailed Aug. 24, 2023.
Office Action for Japanese Application No. 2022-075244 mailed Oct. 20, 2023.

* cited by examiner

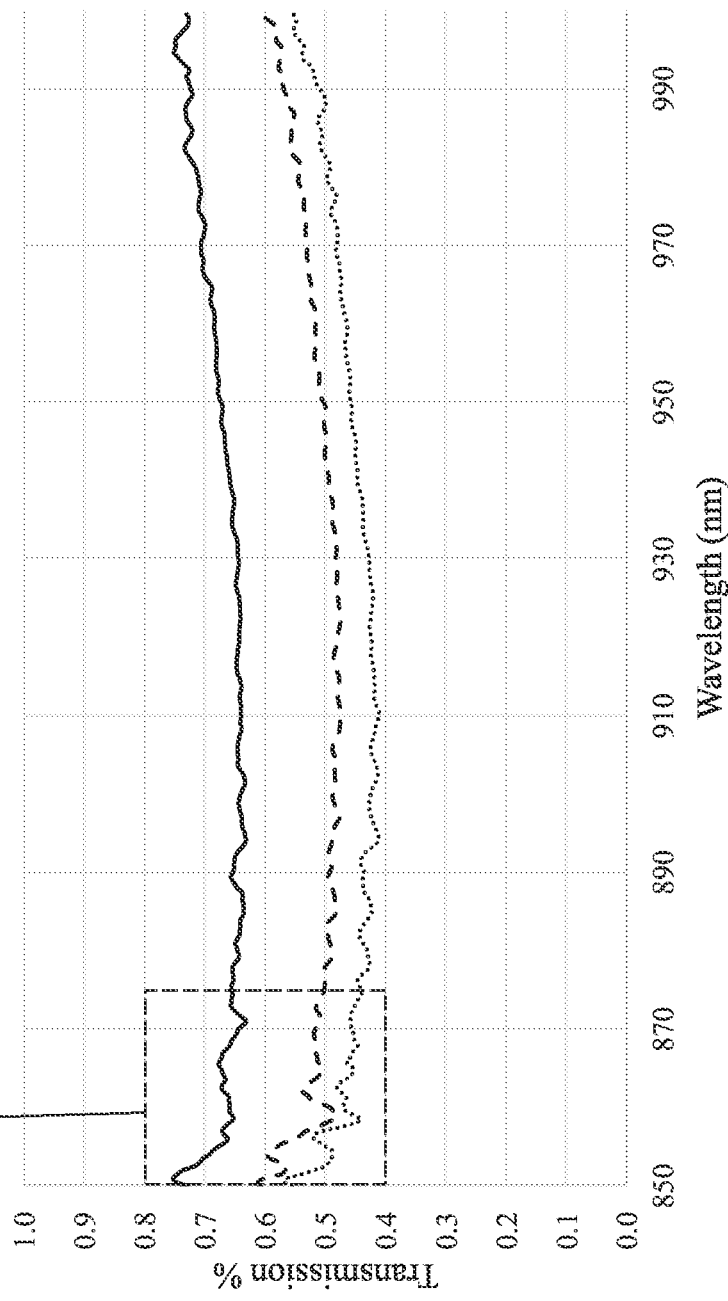
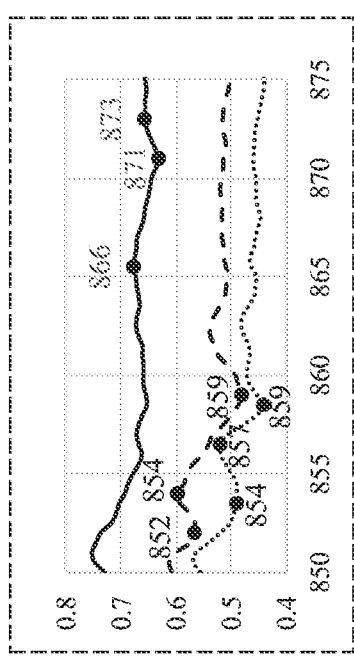
FIG. 9

BODILY EMISSION ANALYSIS

CROSS-REFERENCE TO RELATED APPLICATIONS

The present application is a continuation of U.S. patent application Ser. No. 17/462,147 to Attar filed Aug. 31, 2021 (published as US 2021/0389250), which is a continuation of U.S. patent application Ser. No. 16/325,632 to Attar filed Feb. 14, 2019 (issued as U.S. Pat. No. 11,467,091), which is the US national phase of International application PCT/IL2017/050966 to Attar (published as WO 18/042431), filed Aug. 30, 2017, entitled "Bodily emission analysis," which claims priority from U.S. Provisional Patent Application No. 62/381,288 to Kapp-Barnea, filed Aug. 30, 2016, entitled "Bodily emission analysis."

The above-referenced applications are incorporated herein by reference.

FIELD OF EMBODIMENTS OF THE INVENTION

Some applications of the present invention generally relate to analysis of bodily emissions. Specifically, some applications of the present invention relate to apparatus and methods for analyzing bodily emissions such as urine and feces.

BACKGROUND

Colorectal cancer is the development of cancer in portions of the large intestine, such as the colon or rectum. Gastric cancer is a malignancy of the stomach. Detection of blood in feces is used as a screening tool for colorectal cancer, as well as for gastric cancer. However, the blood is often occult blood, i.e., blood that is not visible. The stool guaiac test is one of several methods that detect the presence of blood in feces, even in cases in which the blood is not visible. A fecal sample is placed on a specially prepared type of paper, called guaiac paper, and hydrogen peroxide is applied. In the presence of blood, a blue color appears on the paper. A patient who is suspected of suffering from colorectal cancer or gastric cancer will typically be assessed using a colonoscopy, a gastroscopy, a sigmoidoscopy, and/or external imaging techniques, such as CT, PET, and/or MRI.

Bladder cancer is a condition in which cancerous cells multiply within the epithelial lining of the urinary bladder. Detection of blood in urine can be useful in screening for bladder cancer. Techniques for detecting blood include placing a test strip that contains certain chemicals into sample of the urine and detecting a color change of the test strip.

SUMMARY OF EMBODIMENTS

In accordance with some applications of the present invention, a bodily emission of a subject that is disposed within a toilet bowl (such as feces or urine) is analyzed automatically. Typically, while the bodily emission is disposed within the toilet bowl, light (which is reflected from the contents of the toilet bowl) is received from the toilet bowl using one or more light sensors, for example, one or more cameras. Using a computer processor, one or more spectral components within the received light that are indicative of light absorption by a component of erythrocytes are detected, by analyzing the received light (e.g., by performing spectral analysis on the received light). In response thereto, the computer processor determines that there is a presence of blood within the bodily emission.

For some applications, the computer processor estimates the amount of the blood within the bodily emission. For some applications, the computer processor determines the location within the gastrointestinal tract that is the source of the blood. For example, the computer processor may determine that time duration over which the blood has aged in anaerobic conditions, by analyzing spectral components within the received light, in order to determine the location within the gastrointestinal tract that is the source of the blood. Alternatively or additionally, the computer processor may analyze the extent to which the blood is spread throughout the feces, and/or a location of the blood within the feces, in order to determine the location within the gastrointestinal tract that is the source of the blood.

The computer processor typically generates an output on an output device (such as a phone, tablet device, server, or personal computer). For some applications, an output is generated indicating that the subject should visit a healthcare professional, and/or indicating a predicted upcoming inflammatory bowel disease episode. For some applications, the output device includes an output component (such as a light (e.g., an LED) or a screen) that is built into the device. Typically, subsequent to the subject emitting the bodily emission into the toilet bowl, the above-described steps are performed without requiring any action to be performed by any person. Thus, for example, the subject is not required to add anything to the toilet bowl in order to facilitate the determination of whether there is blood in the emission.

For some applications, the apparatus analyzes and logs the results of multiple bodily emissions of the subject over an extended period of time, e.g., over more than one week, or more than one month. Typically, in this manner, the apparatus is configured to screen for the presence of early stage cancer and/or polyps, which characteristically bleed only intermittently. For some applications, the apparatus compares the amount of blood that is detected in bodily emissions (e.g., feces), over a period of time, to a threshold amount.

For some applications, the apparatus and methods described herein are used to detect microorganisms within feces, and/or to detect changes therein over time. Alternatively or additionally, the apparatus and methods described herein are used to detect and classify white blood cells within feces, and/or to detect changes therein over time.

There is therefore provided, in accordance with some applications of the present invention, apparatus for use with feces of a subject that are disposed within a toilet bowl, and an output device, the apparatus including:
  one or more light sensors that are configured to receive light from the toilet bowl, while the feces are disposed within the toilet bowl; and
  a computer processor configured to:
    analyze the received light;
    in response thereto, determine that there is a presence of blood within the feces, and determine a source of the blood from within the subject's gastrointestinal tract; and
    generate an output on the output device, at least partially in response thereto.

In some applications, the computer processor is configured to determine the source of the blood by measuring an extent to which the blood is spread throughout the feces. In some applications, the computer processor is configured to determine the source of the blood by measuring a location of the blood within the feces.

In some applications, the computer processor is configured to generate an output by generating an output indicating that the subject should visit a healthcare professional. In some applications, the computer processor is configured to generate an output by generating an output indicating a predicted upcoming inflammatory bowel disease episode.

In some applications, the computer processor is configured to determine the source of the blood from within the subject's gastrointestinal tract by measuring intensities of at least first and second spectral components within the received light, and normalizing the measured intensity of the first spectral component with respect to the measured intensity of the second spectral component.

In some applications, the computer processor is configured to measure the intensity of the first spectral component by measuring a first spectral component, within the received light, that is centered around a wavelength of between 590 nm and 1000 nm, and the computer processor is configured to measure the intensity of the second spectral component by measuring a second spectral component, within the received light, that is centered around a wavelength of between 520 and 590 nm.

In some applications, the computer processor is configured to measure the intensity of the first spectral component by measuring a first spectral component, within the received light, that is centered around a wavelength of between 480 nm and 520 nm, and the computer processor is configured to measure the intensity of the second spectral component by measuring a second spectral component, within the received light, that is centered around a wavelength of between 520 and 590 nm.

In some applications, the computer processor is configured to normalize the measured intensity of the first spectral component with respect to the measured intensity of the second spectral component by calculating a ratio between the measured intensity of the first spectral component and the measured intensity of the second spectral component.

In some applications, the computer processor is configured to calculate the ratio between the measured intensity of the first spectral component and the measured intensity of the second spectral component by calculating a ratio between a measured intensity of a first spectral component, within the received light, that is centered around a wavelength of between 480 nm and 520 nm, and a measured intensity of a second spectral component, within the received light, that is centered around a wavelength of between 520 and 590 nm.

In some applications, the computer processor is configured to calculate the ratio between the measured intensity of the first spectral component and the measured intensity of the second spectral component by calculating a ratio between a measured intensity of a first spectral component, within the received light, that is centered around a wavelength of between 590 nm and 1000 nm, and a measured intensity of a second spectral component, within the received light, that is centered around a wavelength of between 520 and 590 nm.

There is further provided, in accordance with some applications of the present invention, a method for use with feces of a subject that are disposed within a toilet bowl, the method including:
receiving light from the toilet bowl using one or more light sensors, while the feces are disposed within the toilet bowl; and
using a computer processor:
analyzing the received light;
in response thereto, determining that there is a presence of blood within the feces, and determining a source of the blood from within the subject's gastrointestinal tract; and
generating an output on an output device, at least partially in response thereto.

There is further provided, in accordance with some applications of the present invention, apparatus for use with a bodily emission of a subject that is disposed within a toilet bowl, and an output device, the apparatus including:
one or more light sensors that are configured to receive light from the toilet bowl, while the bodily emission is disposed within the toilet bowl; and
a computer processor configured to:
detect a set of three or more spectral components that have a characteristic relationship with each other in a light spectrum of a microorganism, by analyzing the received light;
in response thereto, determine that there is a presence of the microorganism within the bodily emission; and
generate an output on the output device, at least partially in response thereto.

In some applications, the bodily emission includes feces, and the computer processor is configured to determine that there is a presence of the microorganism within the bodily emission by determining that there is a presence of the microorganism within the feces. In some applications, the bodily emission includes urine, and the computer processor is configured to determine that there is a presence of the microorganism within the bodily emission by determining that there is a presence of the microorganism within the urine.

In some applications, the computer processor is configured to detect the set of three or more spectral components that have the characteristic relationship with each other in the light spectrum of the microorganism by detecting one or more spectral components that are due to fluorescence of the microorganism.

In some applications, the computer processor is configured to generate an output by generating an output indicating that the subject should visit a healthcare professional. In some applications, the computer processor is configured to generate an output by generating an output indicating a predicted upcoming inflammatory bowel disease episode.

There is further provided, in accordance with some applications of the present invention, a method for use with a bodily emission of a subject that is disposed within a toilet bowl, the method including:
while the bodily emission is disposed within the toilet bowl, receiving light from the toilet bowl using one or more light sensors;
using a computer processor:
detecting a set of three or more spectral components that have a characteristic relationship with each other in a light spectrum of a microorganism, by analyzing the received light;
in response thereto, determining that there is a presence of the microorganism within the bodily emission; and
generating an output on an output device, at least partially in response thereto.

There is further provided, in accordance with some applications of the present invention, apparatus for use with a bodily emission of a subject that is disposed within a toilet bowl, and an output device, the apparatus including:
one or more light sensors that are configured to receive light from the toilet bowl, while the bodily emission is disposed within the toilet bowl; and a computer processor configured to:
  detect one or more spectral components that are characteristic spectral components at which a given microorganism emits fluorescent light, by analyzing the received light;
  in response thereto, determine that there is a presence of the microorganism within the bodily emission; and
  generate an output on the output device, at least partially in response thereto.

In some applications, the bodily emission includes feces, and the computer processor is configured to determine that there is a presence of the microorganism within the bodily emission by determining that there is a presence of the microorganism within the feces. In some applications, the bodily emission includes urine, and the computer processor is configured to determine that there is a presence of the microorganism within the bodily emission by determining that there is a presence of the microorganism within the urine.

In some applications, the computer processor is configured to detect three or more spectral components that are characteristic spectral components at which the given microorganism emits fluorescent light, the three or more spectral components having a characteristic relationship with each other in a fluorescent spectrum of the microorganism.

In some applications, the computer processor is configured to generate an output by generating an output indicating that the subject should visit a healthcare professional. In some applications, the computer processor is configured to generate an output by generating an output indicating a predicted upcoming inflammatory bowel disease episode.

There is further provided, in accordance with some applications of the present invention, a method for use with a bodily emission of a subject that is disposed within a toilet bowl, the method including:
  receiving light from the toilet bowl using one or more light sensors, while the bodily emission is disposed within the toilet bowl; and
  using a computer processor:
    detecting one or more spectral components that are characteristic spectral components at which a given microorganism emits fluorescent light, by analyzing the received light;
    in response thereto, determining that there is a presence of the microorganism within the bodily emission; and
    generating an output on an output device, at least partially in response thereto.

There is further provided, in accordance with some applications of the present invention, apparatus for use with a bodily emission of a subject that is disposed within a toilet bowl, and an output device, the apparatus including:
  one or more light sensors that are configured to receive light from the toilet bowl, while the bodily emission is disposed within the toilet bowl; and
  a computer processor configured to:
    detect one or more spectral components that are characteristic spectral components at which white blood cells emit fluorescent light, by analyzing the received light;
    in response thereto, determine that there is a presence of white blood cells within the bodily emission; and
    generate an output on the output device, at least partially in response thereto.

In some applications, the bodily emission includes feces, and the computer processor is configured to determine that there is a presence of the white blood cells within the bodily emission by determining that there is a presence of the white blood cells within the feces. In some applications, the bodily emission includes urine, and the computer processor is configured to determine that there is a presence of the white blood cells within the bodily emission by determining that there is a presence of the white blood cells within the urine.

In some applications, the computer processor is configured to detect three or more spectral components that are characteristic spectral components at which the white blood cells emits fluorescent light, the three or more spectral components having a characteristic relationship with each other in a fluorescent spectrum of the white blood cells.

In some applications, the computer processor is further configured to classify the detected white blood cells as a given type of white blood cell.

In some applications, the computer processor is configured to generate an output by generating an output indicating that the subject should visit a healthcare professional. In some applications, the computer processor is configured to generate an output by generating an output indicating a predicted upcoming inflammatory bowel disease episode.

There is further provided, in accordance with some applications of the present invention, a method for use with a bodily emission of a subject that is disposed within a toilet bowl, the method including:
  receiving light from the toilet bowl using one or more light sensors, while the bodily emission is disposed within the toilet bowl; and
  using a computer processor:
    detecting one or more spectral components that are characteristic spectral components at which white blood cells emit fluorescent light, by analyzing the received light;
    in response thereto, determining that there is a presence of white blood cells within the bodily emission; and
    generating an output on an output device, at least partially in response thereto.

There is further provided, in accordance with some applications of the present invention, apparatus for use with a bodily emission of a subject that is disposed within a toilet bowl, and an output device, the apparatus including:
  one or more light sensors that are configured to receive light from the toilet bowl, while the bodily emission is disposed within the toilet bowl; and
  a computer processor configured to:
    detect a set of three or more spectral components that have a characteristic relationship with each other in a light absorption spectrum of a component of blood, by analyzing the received light;
    in response thereto, estimate an amount of blood within the bodily emission; and
    generate an output on the output device, at least partially in response thereto.

In some applications, the computer processor is configured to estimate the amount of blood within the bodily emission by estimating a concentration of blood within the bodily emission. In some applications, the computer processor is configured to estimate the amount of blood within the bodily emission by estimating a volume of blood within the bodily emission.

In some applications, the bodily emission includes feces, and the computer processor is configured to estimate the amount of blood within the bodily emission by estimating an amount of blood within the feces. In some applications, the bodily emission includes urine, and the computer processor is configured to estimate the amount of blood within the bodily emission by estimating an amount of blood within the urine.

In some applications, the computer processor is configured to detect the set of three or more spectral components that have the characteristic relationship with each other in the light absorption spectrum of the component of blood by detecting a set of three or more spectral components that have a characteristic relationship with each other in a light absorption spectrum of a component of blood selected from the group consisting of: oxyhemoglobin, deoxyhemoglobin, methemoglobin, carboxyhemoglobin, heme, and platelets.

There is further provided, in accordance with some applications of the present invention, a method for use with a bodily emission of a subject that is disposed within a toilet bowl, the method including:

while the bodily emission is disposed within the toilet bowl, receiving light from the toilet bowl using one or more light sensors;

using a computer processor:
  detecting a set of three or more spectral components that have a characteristic relationship with each other in a light absorption spectrum of a component of blood, by analyzing the received light;
  in response thereto, estimating an amount of blood within the bodily emission; and
  generating an output on an output device, at least partially in response thereto.

The present invention will be more fully understood from the following detailed description of embodiments thereof, taken together with the drawings, in which:

BRIEF DESCRIPTION OF THE DRAWINGS

FIG. 9 shows infrared light transmission spectra that were recorded from respective strains of bacteria, in an experiment that was conducted in accordance with some applications of the present invention;

DETAILED DESCRIPTION OF EMBODIMENTS

Figure 1:
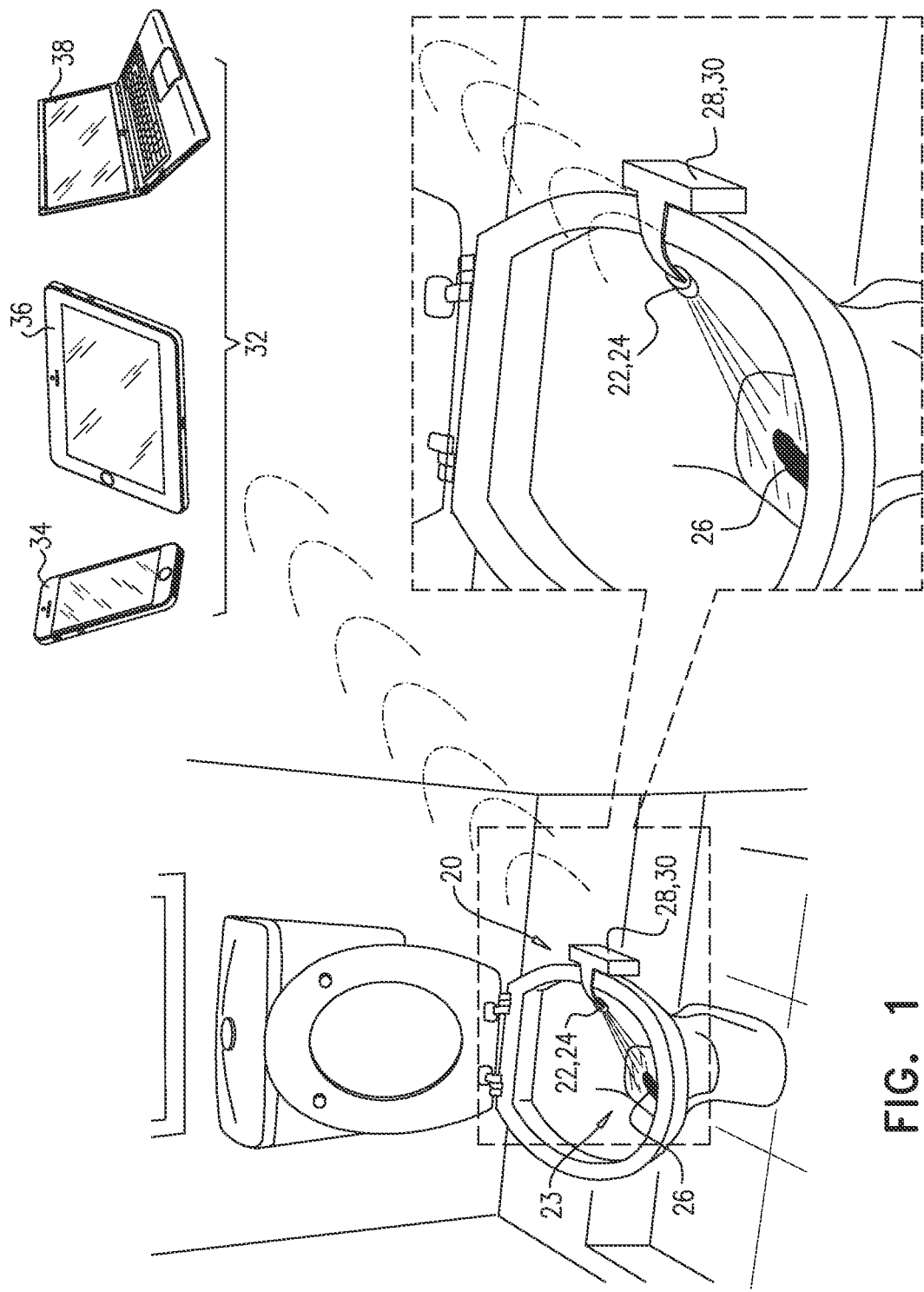
FIG. 1 is a schematic illustration of apparatus for analyzing a bodily emission, in accordance with some applications of the present invention.

Reference is now made to FIG. 1, which is a schematic illustration of apparatus 20 for analyzing a bodily emission, in accordance with some applications of the present invention. As shown, apparatus 20 typically includes a sensor module 22, which is placed inside a toilet bowl 23. For some applications (not shown), the sensor module (and/or additional components of the apparatus) is integrated into the toilet bowl. The sensor module includes an imaging component 24, which in turn includes one or more light sensors that are configured to receive light from bodily emissions (typically, urine or feces 26) that were emitted by the subject and are disposed inside the toilet bowl. For example, the light sensors may include a spectrometer, or may include one or more cameras, as described in further detail hereinbelow. A computer processor analyzes the received light, and determines whether there is a presence of blood inside the bodily emission. Typically, the computer processor detects one or more spectral components within the received light that are indicative of light absorption by a component of erythrocytes, by analyzing the received light (e.g., by performing spectral analysis on the received light). (Such spectral components are referred to herein as examples of a blood signature, since certain combinations of such components, as described herein, are indicative of the presence of blood.) Further typically, the steps of receiving light, analyzing the received light, and determining whether there is a presence of blood inside the bodily emission are performed without requiring any action to be performed by any person (e.g., the user, a caregiver, or a healthcare professional) subsequent to the subject emitting the bodily emission into the toilet bowl.

For some applications, apparatus 20 includes a power source 28 (e.g., a battery pack), that is disposed outside the toilet bowl inside a housing 30, as shown in FIG. 1. Alternatively or additionally, the sensor module is connected to mains electricity (not shown). Typically, the power source and sensor module 22 are connected wiredly (as shown), or wirelessly (not shown). In accordance with respective applications, the computer processor that performs the above described analysis is disposed inside the toilet bowl (e.g., inside the same housing as the sensor module), inside housing 30, or remotely. For example, as shown, the sensor module may communicate wirelessly with a user interface device 32 that includes a computer processor. Such a user interface device may include, but is not limited to, a phone 34, a tablet computer 36, a laptop computer 38, or a different sort of personal computing device. The user interface device typically acts as both an input device and an output device, via which the user interacts with sensor module 22. The sensor module may transmit data to the user interface device and the user interface device computer processor may run a program that is configured to analyze the light received by the imaging module and to thereby detect whether there is a presence of blood inside the subject's bodily emission.

For some applications, sensor module 22 and/or the user interface device communicates with a remote server. For example, the apparatus may communicate with a physician or an insurance company over a communication network without intervention from the patient. The physician or the insurance company may evaluate the results and determine whether further testing or intervention is appropriate for the patient. For some applications, data relating to the received light are stored in a memory (such as memory 46 described hereinbelow). For example, the memory may be disposed inside the toilet bowel (e.g., inside the sensor unit), inside housing 30, or remotely. Periodically, the subject may submit the stored data to a facility, such as a healthcare facility (e.g., a physician's office, or a pharmacy) or an insurance company, and a computer processor at the facility may then perform the above-described analysis on a batch of data relating to a plurality of bodily emissions of the subject that were acquired over a period of time.

It is noted that the apparatus and methods described herein include a screening test in which the subject is not required to physically touch the bodily emission. Furthermore, the subject is typically only required to touch any portion of the dedicated sensing apparatus periodically, for example, in order to install the device, or to change or recharge the device batteries. (It is noted that the subject may handle the user interface device, but this is typically a device (such as a phone) that subject handles even when not using the sensing apparatus.) Further typically, the apparatus and methods described herein do not require adding anything to the toilet bowl subsequent to the subject emitting a bodily emission into the toilet bowl, in order to facilitate the spectral analysis of the emission, and/or a determination that the emission contains blood. For some applications, the subject is not required to perform any action after installation of the apparatus in the toilet bowl. The testing is automatic and handled by the apparatus, and monitoring of the subject's emissions is seamless to the subject and does not require compliance by the subject, so long as no abnormality is detected.

Typically, subsequent to the subject emitting a bodily emission into the toilet bowl (and typically once the subject has finished excreting the bodily emission, and the bodily emission is at least partially disposed within the water of the toilet bowl), the bodily emission is imaged by receiving reflected and/or transmitted light from the toilet bowl, without requiring any action to be performed by any person subsequent to the emission. For some applications, the bodily emission is analyzed during the emission of the bodily emission into the toilet bowl. Typically, the computer processor (a) analyzes (e.g., spectrally analyzes) the received light, (b) in response thereto, determines whether that there is a presence of blood within the bodily emission (and/or performs the additional functionalities described herein with respect to the bodily emission), and (c) generates an output at least partially in response thereto, all without requiring any action to be performed by any person subsequent to the emission. It is noted that for some applications, an input is requested from the subject, via the user interface device, if an indication of the presence of blood in the bodily emission is detected, as described in further detail hereinbelow. However, even for such applications, it is determined that there is a presence of blood based upon the automatic spectral analysis, and the user input is used in order to determine the source of the blood, and/or to determine whether or not the source of the blood is a cause for concern.

For some applications, for each emission of the subject, in the case of positive signal, the apparatus reports the finding to the patient via an output device, e.g., via user interface device 32. For some applications, the output device includes an output component (such as a light (e.g., an LED) or a screen) that is built into apparatus 20. For some applications, if the analysis of the bodily emission indicates that there is blood present inside the emission, the computer processor drives the user interface to request an input from the subject, by asking the user some verification questions. For example, the user interface device may ask the user "Did you eat red meat in the 24 hours prior to your recent stool emission?" since red meat consumption may cause a false positive due to the meat containing blood. Alternatively or additionally, the user interface device may ask the user "Have you used aspirin or other non-steroidal anti-inflammatory drugs?" since the intake of such drugs has been shown to cause bleeding in the stomach or gastrointestinal tract of susceptible individuals. For some applications, the data are analyzed locally but the results are transmitted to the healthcare provider or to insurance carrier over a network connection.

For some applications, the apparatus monitors bodily emissions of the subject over an extended period of time, e.g., over more than one week, or more than one month. Typically, in this manner, the apparatus is configured to screen for the presence of malignancies and/or polyps, which characteristically bleed only intermittently. For some applications, the apparatus compares the amount of blood that is detected in bodily emissions (e.g., feces), over a period of time, to a threshold amount. It is known that there is a level of normal, physiologic, non-pathogenic gastro-intestinal bleeding, which has been estimated as averaging less than 2 ml/day. Intestinal bleeding that is greater than 2 ml/day is considered abnormal. (It is noted that the precise amount that is considered abnormal may differ for each person, depending, for example, on age and sex. Thus, for example, for mature women, normal blood concentration in stool may be considered to be below 64 microgram/gram, whereas for mature males anything above 20 microgram/gram may be considered abnormal.) Therefore, for some applications, the threshold is calibrated to enhance specificity of the sensing, such that alerts will not be generated if the level of bleeding is consistent with normal, physiologic, non-pathogenic gastro-intestinal bleeding, but will generate an alert, if, for example, the level of bleeding is indicative of the presence of cancer and/or polyps.

For some applications, the computer processor which analyzes the received light utilizes machine learning techniques, such as anomaly detection and/or outlier detection. For example, the computer processor may be configured to perform individualized anomaly detection or outlier detection that learns the patterns of output signals from each subject and detects abnormal changes in the characteristic blood signature of the subject. As described hereinabove, for some applications, the computer processor that performs the analysis is remote from and/or separate from the sensor module. For some applications, the sensor module is disposable, but even after disposal of the sensor module the computer processor has access to historic data relating to the subject, such that the historic data can be utilized in the machine learning techniques.

Figure 2:
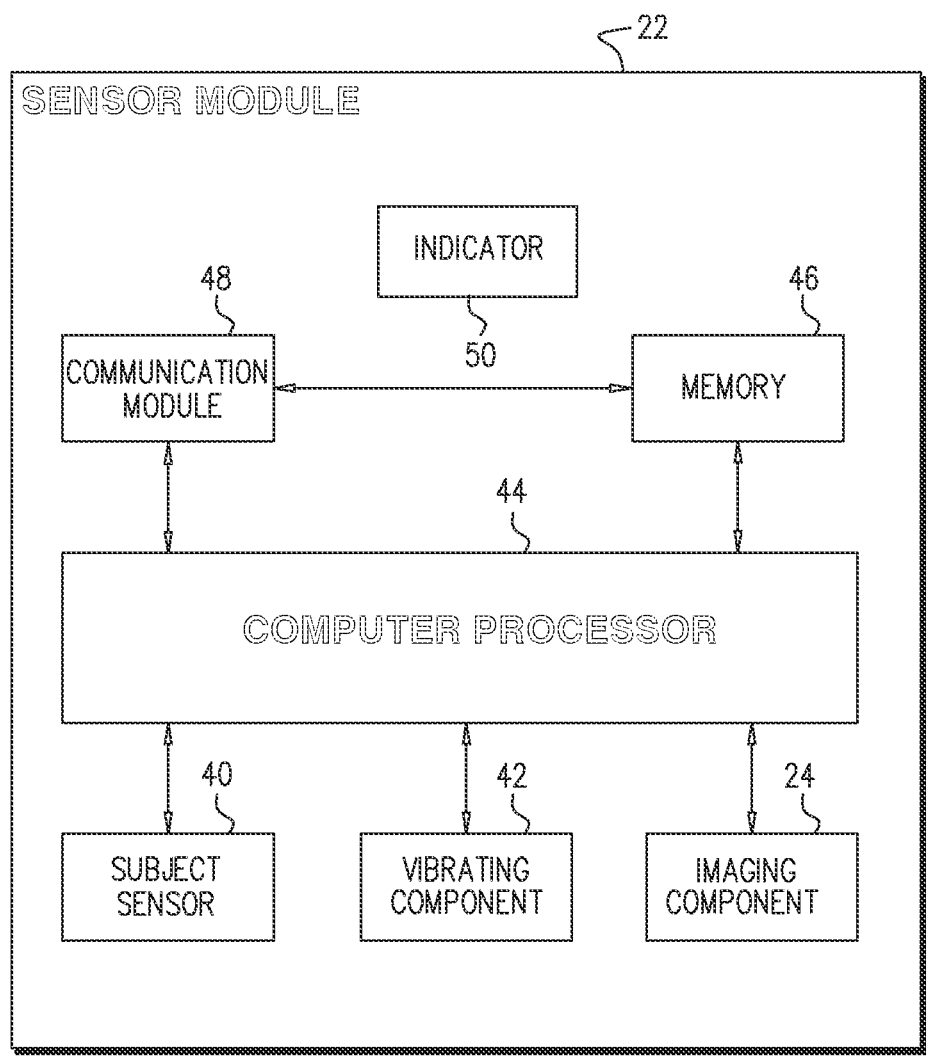
FIG. 2 is a block diagram that schematically illustrates components of a sensor module, in accordance with some applications of the present invention.

Reference is now made to FIG. 2, which is a block diagram that schematically illustrates components of sensor module 22, in accordance with some applications of the present invention. As described hereinabove, sensor module is typically disposed inside a toilet bowl. Further typically, the sensor module includes an imaging component, which in turn includes one or more light sensors that are configured to receive light from bodily emissions that were emitted by the subject and are disposed inside the toilet bowl. The imaging component is described in further detail hereinbelow, with reference to FIGS. 3A-B. Typically, the sensor module is housed in a water-resistant housing. Further typically, the face of the sensor module underneath which the imaging component is mounted is covered with a transparent, water-resistant cover. It is noted that FIG. 1 shows the sensor module disposed above the water level of the water within the toilet bowl. However, for some applications, at least a portion of the sensor module (e.g., the entire sensor module) is submerged within the water in the toilet bowl.

For some applications, the sensor module includes a subject sensor 40. The subject sensor is configured to detect when a subject is on or in the vicinity of the toilet, and/or if the subject has defecated and/or urinated into the toilet bowl. For example, the subject sensor may include a motion sensor, configured to sense the motion of feces, urine, the subject, or the water in the toilet bowl. Alternatively or additionally, the subject sensor may include a light sensor configured to detect when the light in the bathroom is switched on, or when the subject sits on the toilet. For some applications, the light sensors that are used for detecting light from the bodily emission are also used for the aforementioned function. For some such applications, the sensor module is configured to be in standby mode most of the time (such that the sensor module uses a reduced amount of power). The sensor module is switched on in response to detecting that the subject is on or in the vicinity of the toilet, and/or that the subject has defecated and/or urinated into the toilet bowl. Typically, the imaging component of the sensor module acquires images in response to detecting that the subject is on or in the vicinity of the toilet, and/or that the subject has defecated and/or urinated into the toilet bowl. For some applications, the subject switches on the sensor module manually.

For some applications, the sensor module includes a vibrating component 42 that is typically configured to vibrate feces that is inside the toilet bowl. The vibrating element may include an ultrasonic vibrator, a mechanical element that is moved by a motor, and/or a pump configured to emit jets of water. The vibrating element is typically configured to break feces into smaller pieces such that blood that is disposed inside the piece of feces becomes visible to the imaging component. It is noted that, for some applications, the vibrating component is disposed in the toilet bowl separately from the sensor module. For some applications, a vibrating component is not used, but apparatus 20 is able to determine whether there is blood present in feces to a sufficient level of specificity, due to the feces breaking upon falling into the toilet bowl and impacting the toilet bowl.

Typically, the sensor module includes a computer processor 44, a memory 46, and a communication module 48. Computer processor 44 is configured to drive the imaging component to perform the functions described herein. For some applications, the computer processor is further configured to perform the analysis functions described herein. For such applications, computer processor 44 typically communicates the results of the analysis (e.g., a positive detection of blood in feces) to a remote device, such as user interface device 32 (FIG. 1), via communication module 48. Alternatively, as described hereinabove, the analysis of the received light may be performed by a remote computer processor, e.g., a computer processor that is part of the user interface device. For such applications, computer processor 44 typically communicates raw imaging data, and/or light signals to the remote computer processor, via communication module 48. For some applications, computer processor stores data in memory 46. The data may include raw data, which may subsequently be retrieved and analyzed, and/or the results of the spectral analysis of the light received by the imaging component. Memory 46 may include a memory card, such as an SD card that can be physically removed. Communication module is typically configured to communicate with external devices (e.g., user interface device 32) using known protocols, such as Wifi, Bluetooth®, ZigBee®, or any near field communication (NFC) protocol.

For some applications, sensor module 22 includes an indicator 50, e.g., a visual indicator (such as an LED light), or an audio indicator (for example, a speaker that is configured to emit a beep), the indicator being configured to indicate to the subject when a sample has been successfully imaged, and/or when data has been successfully transmitted to a remote device, such as user interface device 32. It is noted that, although not shown, the indicator typically interacts with other components of the sensor module such as the computer processor and/or the communication module.

Figure 3A:
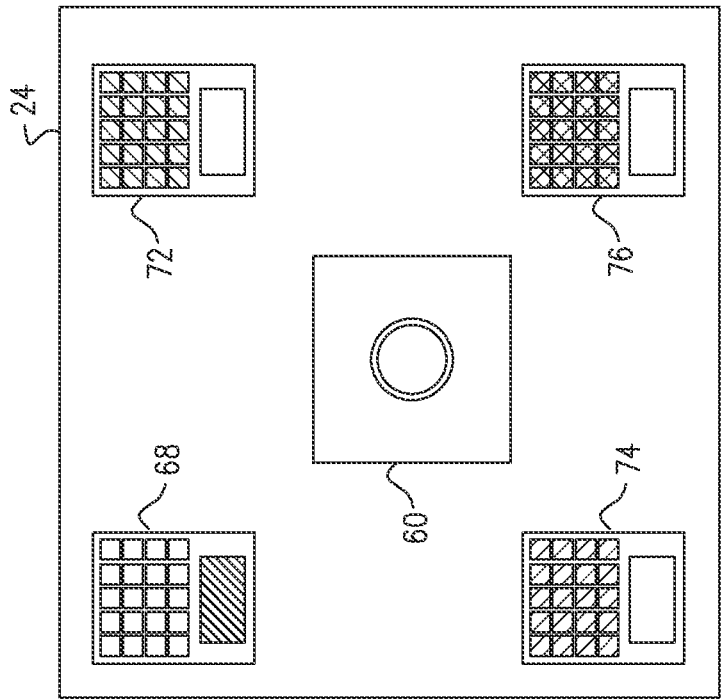
FIGS. 3A and 3B are schematic illustrations of components of an imaging component of the sensor module, in accordance with respective applications of the present invention.
Figure 3B:
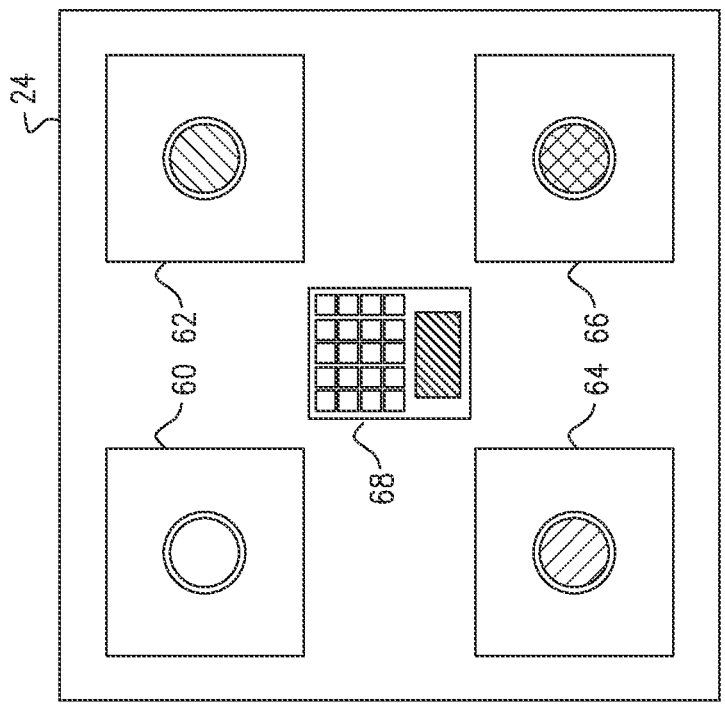

Reference is now made to FIG. 3A-B are schematic illustrations of components of imaging component 24, in accordance with respective applications of the present invention. Imaging component 24 is typically disposed on a face of sensor module 22 that faces toward the water in the toilet bowl. FIGS. 3A-B is schematic illustrations of the aforementioned face of the sensor module.

As described in further detail hereinbelow, typically in order to detect a blood signature within a bodily emission, particular spectral bands within light that is reflected from and/or transmitted by the bodily emission are detected. Typically, the spectral bands are centered around a wavelength that is in the range of 530 nm to 785 nm (e.g., between 530 nm and 600 nm). Further typically, two or more spectral bands are detected that are centered around approximately 540 nm, 565 nm, and 575 nm. For some applications, other spectral bands that are indicative of the presence of blood are measured. For example, a spectral band centered around approximately 425 nm (e.g., between 420 and 430 nm) and/or a spectral band centered around approximately 500 nm (e.g., between 490 and 510 nm) may be detected. The widths of the spectral bands are typically greater than 3 nm (e.g., greater than 5 nm, or greater than 8 nm), and/or less than 40 nm (e.g., less than 20 nm, or 12 nm), e.g., between 3 and 40 nm, between 5 and 20 nm or between 8 and 12 nm. A spectral band that is described herein as being centered around approximately a given spectral value should be interpreted as including a spectral band centered around the given value plus/minus 5 nm.

Referring to FIG. 3A, for some applications, imaging component 24 of sensor module 22 includes a light source 68 (e.g., an LED light emitter, or a different type of light) that emits white light. In addition, the imaging module includes two or more cameras, which act as light sensors.

The two or more cameras may include a color camera 60, and/or a monochrome camera that includes a filter such as to detect a first one of the above-described spectral bands (camera 62), a second one of the above-described spectral bands (camera 64), and/or a third one of the above-described spectral bands (camera 66). The cameras act as light sensors of apparatus 20, and the light source acts to illuminate the toilet bowl and the bodily emission. For some applications, all four cameras are used in the imaging component. For some applications, a different type of light sensor (e.g., a spectrometer) is used as alternative to, or in addition to, cameras.

For some applications, the computer processor of apparatus 20 is configured to identify spectral components within respective portions of the bodily emission, by analyzing respective pixels within the images acquired by the cameras, on an individual basis. In order to identify the spectral components of a given portion of the bodily emission, the computer processor determines a correspondence between pixels of images that were acquired by respective cameras. Typically, irrespective of how many cameras are used, all of the cameras are disposed in close proximity to one another, e.g., such that all of the cameras are disposed within an area of less than 10 square centimeters (e.g., an area of less than 5 square centimeters, or an area of less than 1 square centimeter). For some applications, using cameras that are disposed in close proximity to one another facilitates determining the correspondence between pixels of images that were acquired by respective cameras.

Referring to FIG. 3B, for some applications, imaging component 24 of sensor module 22 includes color camera 60, and includes two or more light sources (e.g., LED lights or other types of lights) that emit light at respective spectral bands. The two or more light sources typically include light source 68 (which as described with reference to FIG. 3A is configured to emit white light) and/or light sources that are configured to emit light at a first one of the above-described spectral bands (light source 72), a second one of the above-described spectral bands (light source 74), and/or a third one of the above-described spectral bands (light source 76). For some applications, narrowband filters are mounted upon one or more of the light sources. The camera acts as a light sensor of apparatus 20, and the light sources act to illuminate the toilet bowl and the bodily emission. For some applications, all four light sources are used in the imaging component.

It is noted that for some applications, the imaging component does not include a light source, and the light sensors of the imaging component (e.g., the cameras) rely upon ambient light. Alternatively, the light source and the light sensors of the imaging component may be disposed on different sides of the toilet bowl from one another. For some applications, the imaging component is configured to detect optical transmission and/or optical reflectance of the bodily emission. Alternatively or additionally, the imaging component is configured to detect optical absorption of the bodily emission. In general, the scope of the present application includes detecting spectral components of the light spectrum of a bodily emission as described herein, by detecting and/or calculating the intensity of the spectral components in optical reflectance, optical transmission, and/or optical absorption spectra of the bodily emission and/or water in the toilet bowl that is in contact with the bodily emission. For some applications, rather than using one or more cameras, which are configured to detect light on a pixel-by-pixel basis, a spectrometer is used to detect the overall spectrum of light that is reflected from the bodily emission, and to analyze the reflected light.

For some applications, color camera 60 is a multispectral camera or a hyperspectral camera. For example, a hyperspectral camera may be used to acquire images of a bodily emission, and the computer processor may analyze the data by generating a hypercube of data that contains two spatial dimensions and one wavelength dimension. The computer processor may determine whether or not there is blood in the bodily emission, by analyzing the hypercube.

It is further noted that the particular arrangements of light sources and light sensors shown in FIGS. 3A-B are examples, and the scope of the present invention includes using alternative or additional arrangements of light sources and/or light detectors. For example, more or fewer than four light sources and/or light sensors may be used. Similarly, the light sources and/or light sensors may be arranged in a different configuration to those shown in FIGS. 3A-B. The scope of the present invention includes using any combination of light sensors and light sources, arranged in any configuration that would facilitate measurements as described herein being performed.

Typically, the light sensors of imaging component 24 of the sensor module 22 acquire images in response to detecting that the subject is on or in the vicinity of the toilet, and/or that the subject has defecated and/or urinated into the toilet bowl, as described hereinabove. For some applications, during the acquisitions of images by camera(s) 60, 62, 64, and/or 66, bursts of images are acquired at given time intervals. For example, a burst may be acquired once every 3 seconds, every 5 second, or every 10 seconds. Each burst of images typically contains between 1 and 8 images, e.g., between 3 and 5 images. Typically, all of the images that are acquired of a given emission are acquired within a total time that is less than 20 seconds, such that there is no substantial movement of the bodily emission between the acquisitions of respective images within each burst. For some applications, the maximum exposure time per image frame is typically 10 ms. Alternatively, the exposure time per image frame may be more than 10 ms, e.g., more than 35 ms.

The apparatus and methods described herein utilize the light reflected back from erythrocytes and collected by light sensors. In some embodiments, this light can be reflected from the ambient light source and in other embodiments a light source is an integral part of the system. In some embodiments, such a light source can be an LED of one or several wavelengths, or a broadband light source with a bandpass filter. As described hereinabove, erythrocytes have a distinct spectral signature, which is reflected from the tested medium and can be detected by light sensors, the signature being referred to herein as the blood signature.

For some applications, the sensor module detects a presence of blood in the bodily emission in response to detecting that the value returned by a mathematical function of the absorption, transmission, and/or reflectance of two or more wavelengths or weighted functions of wavelengths return a certain value. As described hereinabove, for some applications, the sensor module transmits the output of the light sensors to user interface device 32 (FIG. 1) and software that is run by a computer processor on the device performs the analysis.

In general, apparatus 20 typically includes illumination source(s) (i.e., light source(s)) for irradiating biological fluids that are excreted from patient and pass in the toilet bowl water. For some applications, radiation (e.g., radiation in the visible light range) is emitted at various wavelengths of interest, to evaluate the optical signature of the specimen. A light detector is positioned with respect to the light source(s) on the opposite side, the same side, or anywhere else in the toilet bowl. For example, the light detectors may face the light source(s) such as to detect light from the light source(s) that passes through the bodily emission, and/or through water in the toilet bowl that is in contact with the bodily emission. It is noted that although some applications of the present invention relate to using the detection of radiation in the visible light range to perform the techniques described herein, the scope of the present invention includes using radiation at any spectral band to perform techniques described here, mutatis mutandis.

For some applications, a white light broadband illumination source is used (e.g., white light source 68), and the light detector may comprise at least two light detectors (e.g., two or more of cameras 60, 62, 64, and 66). Each light detector may comprise a different filter for collecting light at a different wavelength, after passing through the biological fluids. The filters may be narrow band filters, interference filters, absorbing filters, or diffractive optical element (DOE) filters.

Figure 4:
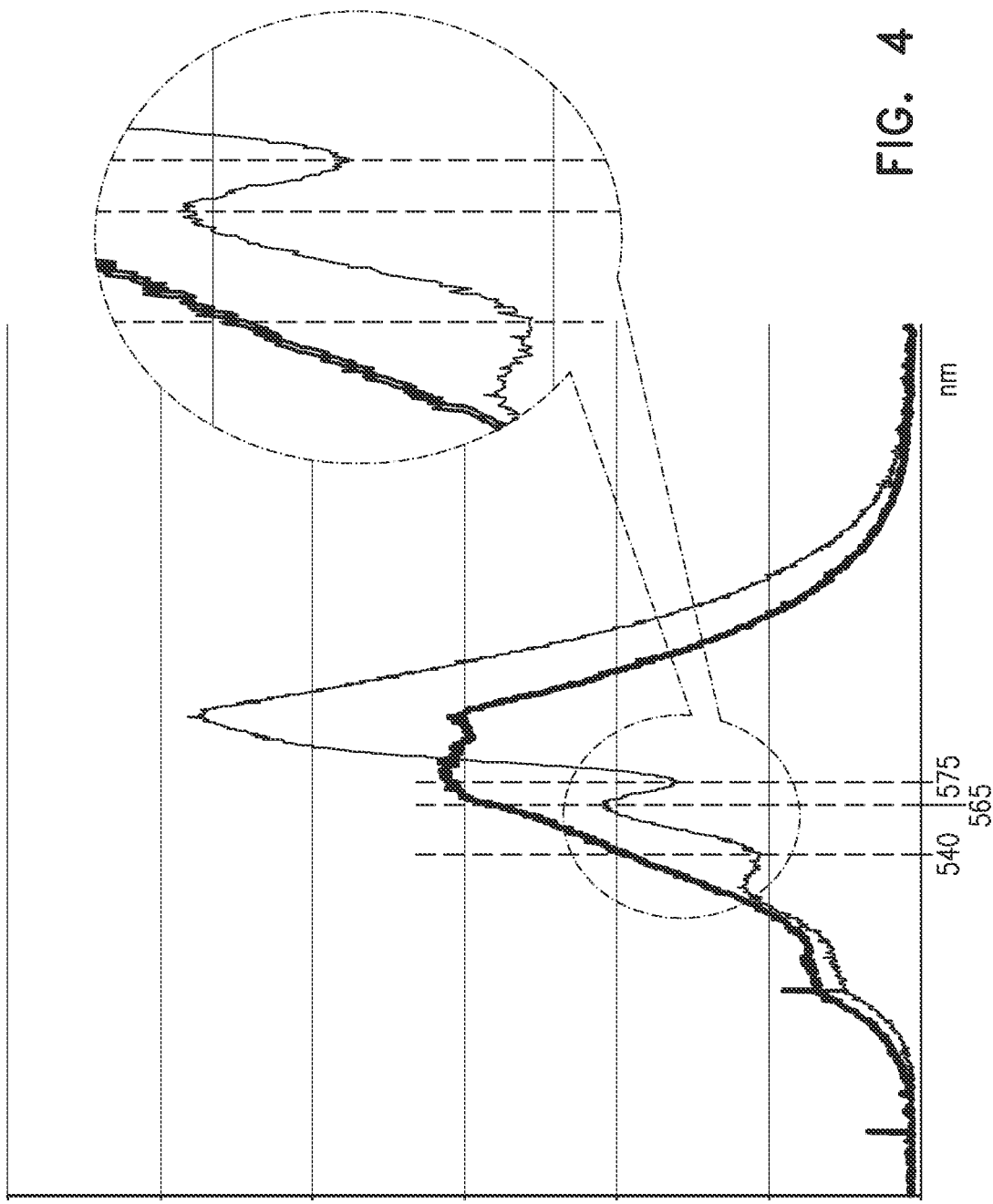
FIG. 4 is a graph showing spectrograms that were recorded from stool samples, in accordance with some applications of the present invention.

Reference is now made to FIG. 4, which is a graph showing spectrograms that were recorded from stool samples, in accordance with some applications of the present invention. A raw human stool sample and a human stool sample into which 0.2 ml of blood had been injected were placed inside a glass container (with dimensions 86×86×90 mm) that contained tap water to a height of about 70 mm (~500 cc of water). White LED light in the range of 400-700 nm and an intensity of approximately 220 lumens was directed into the container, and spectrograms of the light that was reflected from the container were acquired using a standard spectrometer.

The thicker curve is the spectrogram that was obtained from the raw stool sample, and the thinner curve is the spectrogram that was obtained from the stool with blood. As may be observed, in the enlarged portion of the graph, the spectrogram that was obtained from the sample that includes blood includes a characteristic trough-peak-trough shape at approximately 540 nm (trough), 565 nm (peak) and 575 nm (trough). This characteristic shape is an example of a blood signature, the shape being indicative of the presence of blood. Specifically, this shape indicates light absorption by oxyhemoglobin, which is present in erythrocytes in the blood.

The above results indicate that a blood signature can be detected within a stool sample under certain conditions. Furthermore, the above results were obtained by using a spectrogram which analyzes the overall spectral profile of the sample. If analyzing the sample on a pixel-by-pixel basis, as is the case in certain applications of the present invention, the blood signature can be expected to be detected with greater sensitivity and specificity.

Figure 5:
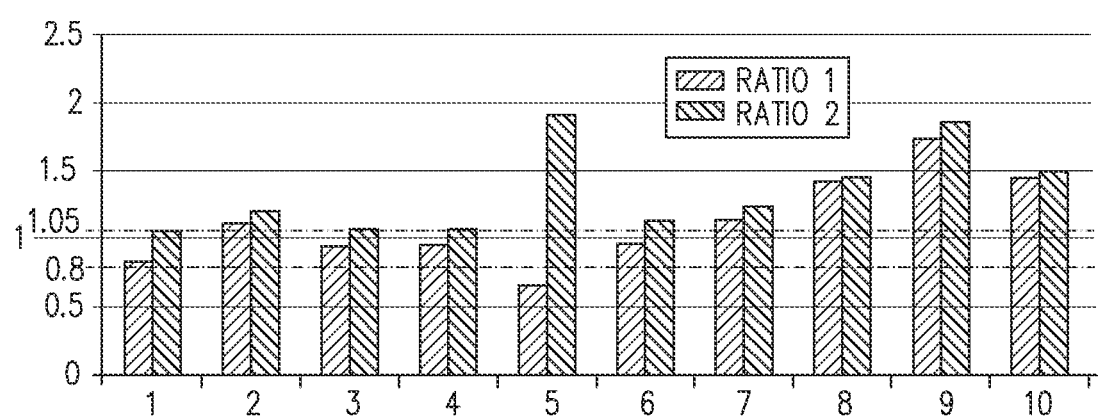
FIG. 5 is a bar-chart showing aspects of spectral components that were recorded from respective samples, during an experiment conducted in accordance with some applications of the present invention.

Reference is now made to FIG. 5, which is a bar-chart showing ratios of spectral components that were recorded from respective samples, during an experiment conducted in accordance with some applications of the present invention. Using the technique described above with respect to FIG. 4, the spectrograms of a plurality of sample were analyzed. The sample included:
1. Fresh beet.
2. Raw fresh meat.
3. A fecal sample that did not contain blood.
4. A second fecal sample that did not contain blood.
5. A mixture of rum and red food colorant.
6. A sample containing feces and 0.2 ml of blood, in which the sample was not mixed.
7. A sample containing feces and 0.2 ml of blood, in which the sample was mixed once by stirring with a rod.
8. A sample containing feces and 0.2 ml of blood, in which the sample was mixed twice by stirring with a rod.
9. A sample containing feces and 5 drops of blood, in which the sample was not mixed.
10. A sample containing feces and 5 drops of blood, in which the sample was mixed twice by stirring with a rod.

The blood was obtained from a blood bank and had been preserved in citrate.

For each of the samples, the received spectrogram was analyzed by calculating two ratios. Ratio 1 was the ratio of the intensity of a 10 nm band centered around 565 nm, to the intensity of a 10 nm band centered around 575 nm (I(565)/I(575)). Ratio 2 was the ratio of the intensity of a 10 nm band centered around 565 nm, to the intensity of a 10 nm band centered around 540 nm (I(565)/I(540)). For the purpose of the experiment, thresholds were set at 1.05 for ratio 1 and 0.8 for ratio 2, such that if ratio 1 would exceed 1.05 and ratio 2 would exceed 0.8, this would be an indication that the sample contains blood. This is because a sample that contains blood would be expected to have a blood signature with a characteristic trough-peak-trough shape at approximately 540 nm (trough), 565 nm (peak) and 575 nm (trough), whereas for a sample that does not contain blood, the slope of the spectrogram could be expected to increase between 540 nm and 575 nm, as shown in the thick curve of FIG. 4. The results are indicated in the bar-chart shown in FIG. 5 and are summarized in the table below:

| Sample | Contained human blood | Both ratios indicate that sample contains blood |
| --- | --- | --- |
| 1 | No | No |
| 2 | No (but contained animal erythrocytes) | Yes |
| 3 | No | No |
| 4 | No | No |
| 5 | No | No |
| 6 | Yes | No |
| 7 | Yes | Yes |
| 8 | Yes | Yes |
| 9 | Yes | Yes |
| 10 | Yes | Yes |

As may be observed based on FIG. 5 and the above table, in general using the above-described ratios and thresholds, blood was detected in feces in four out of five cases. Using the above-described ratios and thresholds, in general, blood was not detected in cases in which blood had not been present in the sample, except for the meat sample (sample 2), which is discussed below. These results indicate that blood can be detected in a bodily emission by spectrally analyzing the emission, using techniques as described herein. Therefore, for some applications of the present invention, spectral bands that are centered around a wavelength that is in the range of 530 nm to 785 nm (e.g., between 530 nm and 600 nm) are detected. Typically, two or more spectral bands are detected that are centered around approximately 540 nm, 565 nm, and 575 nm. The widths of the spectral bands are typically greater than 3 nm (e.g., greater than 5 nm, or greater than 8 nm), and/or less than 40 nm (e.g., less than 20 nm, or less than 12 nm), e.g., between 3 and 40 nm, between 5 and 20 nm, or between 8 and 12 nm. For some applications, one or more ratios of the intensities of the aforementioned spectral bands with respect to one another are determined. For example, the ratio of the intensity of the spectral band that is centered around approximately 565 nm to that of the band centered around approximately 575 nm (or vice versa) may be determined, and/or the ratio of the intensity of the spectral band that is centered around approximately 565 nm to that of the band centered around approximately 540 nm (or vice versa) may be determined. For some applications, a different relationship between the intensities of the aforementioned spectral bands with respect to one another is determined. For some applications, a relationship between a parameter of the respective spectral bands other than intensity is determined. For some applications, other spectral bands that are indicative of the presence of blood are measured. For example, results of experiments performed by the inventors upon whole blood within water indicated that there is a trough in the reflectance spectrum at approximately 425 nm. In the experiment described with reference to FIG. 5, some of the fecal samples with blood exhibited peaks in their reflectance spectra at approximately 500 nm. Therefore, for some applications, a spectral band centered around approximately 425 nm (e.g., between 420 and 430 nm) and/or a spectral band centered around approximately 500 nm (e.g., between 490 and 510 nm) is detected.

It is noted that the results shown in FIG. 5 and summarized in the above table reflect a portion of the samples that were analyzed. In general, there were no false positives, except for when the meat sample was analyzed. This is to be expected, since raw fresh meat has residues of animal blood, which dissolves in the water. In accordance with some applications of the present invention, such false positives are reduced by asking the subject questions, such as whether the subject ate red meat within a given times interval of defecating, as described hereinabove.

False negatives were found when blood was injected into solid feces and did not reach the water (which was the case in sample 6). In accordance with some applications of the present invention, such false negatives are reduced by mixing, vibrating, and/or agitating feces inside the toilet bowl, in accordance with techniques described herein. It is noted that in the experiment, blood was mixed with the stool when the stool was disposed inside the glass container. Typically, when a person defecates into a toilet bowl, the feces are agitated by virtue of the feces falling into and impacting the toilet bowl. Therefore, for some applications of the present invention, no active agitation is provided to the feces disposed in the toilet bowl. In addition, there were false negatives (not shown in FIG. 5) in cases in which blood with beet was used as the sample. For some applications of the present invention, such false negatives are reduced by using greater light intensity than was used in the above-described experiment. It is further noted that since, in accordance with some applications, the analysis of bodily emissions is performed over a period of time, if hidden blood is missed in some emissions, it is likely to be detected in others.

Figure 6:
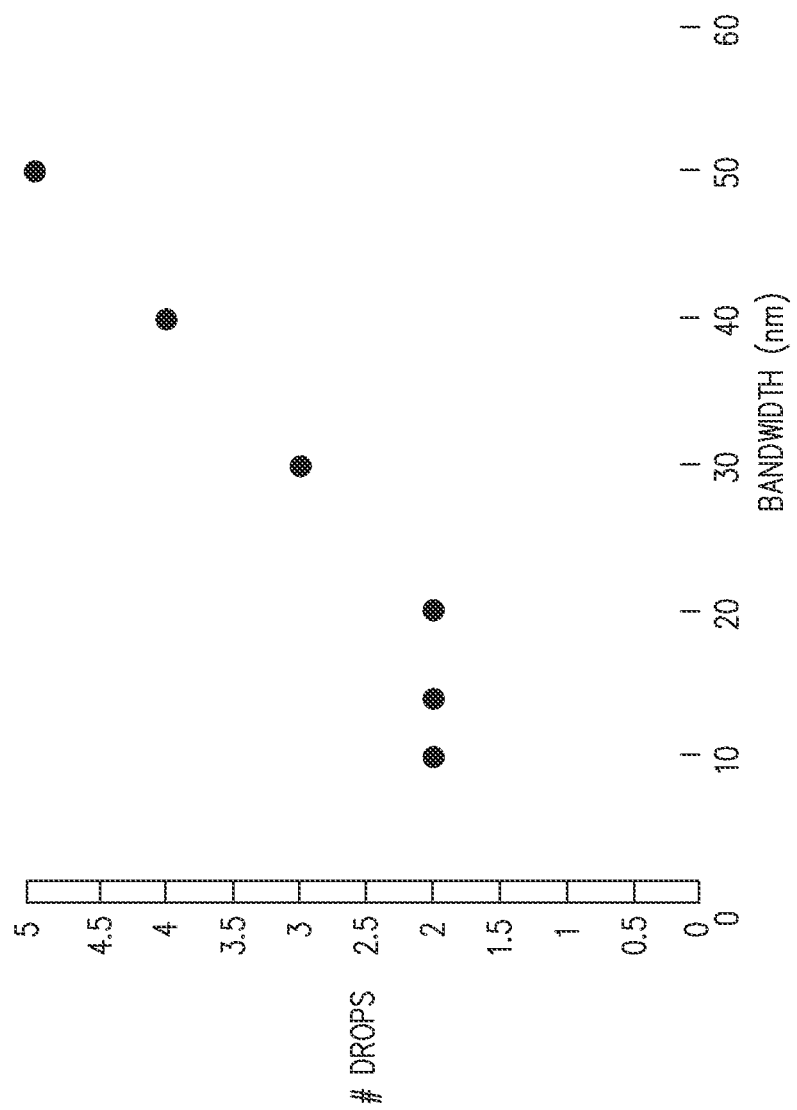
FIG. 6 is a graph showing the results of an experiment that was performed, in accordance with some applications of the present invention.

Reference is now made to FIG. 6, which is a graph showing the results of a simulation that was performed, in accordance with some applications of the present invention. Spectrograms of (a) feces and (b) five drops of blood obtained in an experiment as described hereinabove were used. The spectrogram of the five drops of blood was divided by five, to simulate the spectrogram of one drop, and to improve signal-to-noise ratio relative the spectrogram of a single drop of blood being used. A simulation was performed in order to artificially mix the spectra, such as to produce the effect of feces mixed with respective amount of blood. The above-described first and second ratios were then calculated for increasing bandwidths of spectral filter. FIG. 6 is a plot showing the minimum number of drops that was detectable for each bandwidth. It may be observed that up until a bandwidth of 20 nm, two drops of blood were detectable, whereas for bandwidths of 30 nm and more, a minimum of three drops of blood were required in order for the blood to be detectable. Therefore, for some applications of the present invention, two or more spectral bands are detected that are centered around approximately 540 nm, 565 nm, and 575 nm, and the widths of the spectral bands are typically greater than 3 nm (e.g., greater than 5 nm, or greater than 8 nm), and/or less than 40 nm (e.g., less than 20 nm, or less than 12 nm), e.g., between 3 and 40 nm, between 5 and 20 nm, or between 8 and 12 nm.

Figure 7:
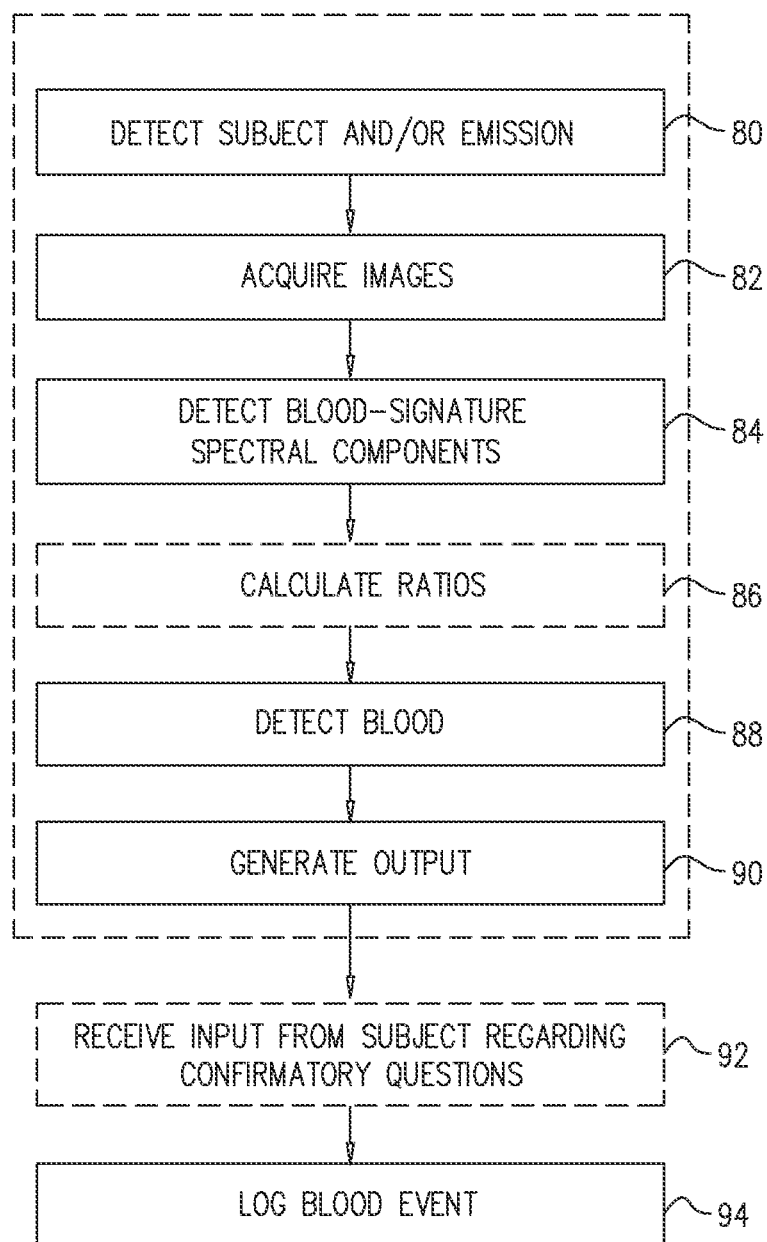
FIG. 7 is a flowchart showing steps that are performed, in accordance with some applications of the present invention.

Reference is now made to FIG. 7, which is a flowchart showing steps of a procedure that is performed, in accordance with some applications of the present invention.

In a first step (step 80), sensor module 22 (e.g., subject sensor 40 of the sensor module) detects a presence of the subject in a vicinity of or on the toilet, and/or detects that a bodily emission has been emitted into the toilet, as described hereinabove with reference to FIG. 2. In response thereto, imaging component 24 of the sensor module receives light from the toilet bowl, typically by acquiring images using one or more cameras (e.g., one or more multispectral cameras, or one or more hyperspectral cameras) (step 82). As noted hereinabove, the scope of the present invention includes receiving radiation at any spectral band, and is not limited to receiving radiation in the visible light range.

The received light is analyzed (e.g. spectrally analyzed) by a computer processor, which may be computer processor 44 of the sensor module, or a different computer processor, as described hereinabove. Typically, spectral bands are detected that centered around a wavelength that is in the range of 530 nm to 785 nm (e.g., between 530 nm and 600 nm). Further typically, blood-signature spectral components are detected (step 84). For example, one or more spectral components within the received light that are indicative of light absorption by a component of erythrocytes (e.g., oxyhemoglobin) may be detected. As described hereinabove, for some applications of the present invention, two or more spectral bands are detected that are centered around approximately 540 nm, 565 nm, and 575 nm. For some applications, other spectral bands that are indicative of the presence of blood are measured. For example, a spectral band centered around approximately 425 nm (e.g., between 420 and 430 nm) and/or a spectral band centered around approximately 500 nm (e.g., between 490 and 510 nm) may be detected. (As noted hereinabove, a spectral band that is described herein as being centered around approximately a given spectral value should be interpreted as including a spectral band centered around the given value plus/minus 5 nm.) For some applications, the detected spectral components are analyzed by calculating ratios of the intensities of respective components with respect to one another (step 86), for example, as described hereinabove. Alternatively or additionally, the spectral components may be analyzed in a different manner (Step 86 is inside a dashed box to indicate that the specific step of calculating ratios is optional.) In response to the spectral analysis, the computer processor detects blood (step 88) and generates an output (step 90), for example, on user interface device 32.

The scope of the present invention includes detecting any spectral components that are indicative of light absorption by a component of erythrocytes, for example spectral components that are indicative of hemoglobin methemoglobin, and/or heme. For some applications, spectral components that are indicative of light absorption of urine and/or feces are detected. For some applications, the computer processor determines whether there is feces and/or urine together with blood, in order to confirm that detected blood is blood that is associated with feces and/or urine and is not from a different source. In addition, the scope of the present invention includes determining any type of relationship between parameters (e.g., intensities) of respective spectral bands within the received light and is not limited to determining ratios between the parameters (e.g., intensities) of the respective spectral bands. Furthermore, even for applications in which ratios 1 and 2 as described hereinabove are calculated, the thresholds that are described as having been used are illustrative, and the scope of the present invention includes using different thresholds to those described hereinabove. For example, for applications in which calibrated light sensors are used, a threshold of more than 1 and/or less than 1.5 (e.g., between 1 and 1.5) may be used for ratio 1 (i.e., I(565)/I(575)), and a threshold of more than 0.7 and/or less than 1 (e.g., between 0.7 and 1) may be used for ratio 2 (i.e., I(565)/I(540)). For applications in which the light sensors are uncalibrated, the ratios may be different.

It is noted that, at this stage, the output may indicate a suspicion of the subject's blood being in the bodily emission. For some applications, in order to confirm the suspicion, the user is requested to provide an input by the user being asked confirmatory questions (the answers to which are typically indicative of the source of the detected blood), as described hereinabove. The computer processor receives the input from the subject regarding the confirmatory questions (step 92). If the input from the user indicates that the detection of blood was not a false positive (that may have been caused, for example, by the subject having eaten red meat), then the computer processor logs that a blood event has occurred (step 94). For example, the computer processor may log the event on memory 46 of the sensor module. For some applications, the blood event is logged even without receiving an input from the user (step 92). For example, the computer processor may account for false positives in a different manner, such as by incorporating a likelihood of false positives into a threshold that is used to monitor blood events over a long-term period. (Step 92 is inside a dashed box to indicate that this step is optional.)

Typically, steps 80-90 of FIG. 7 (the steps inside the large dashed box) are performed without requiring any action by the subject or any other person, subsequent to the subject emitting a bodily emission into the toilet bowl.

Figure 8:
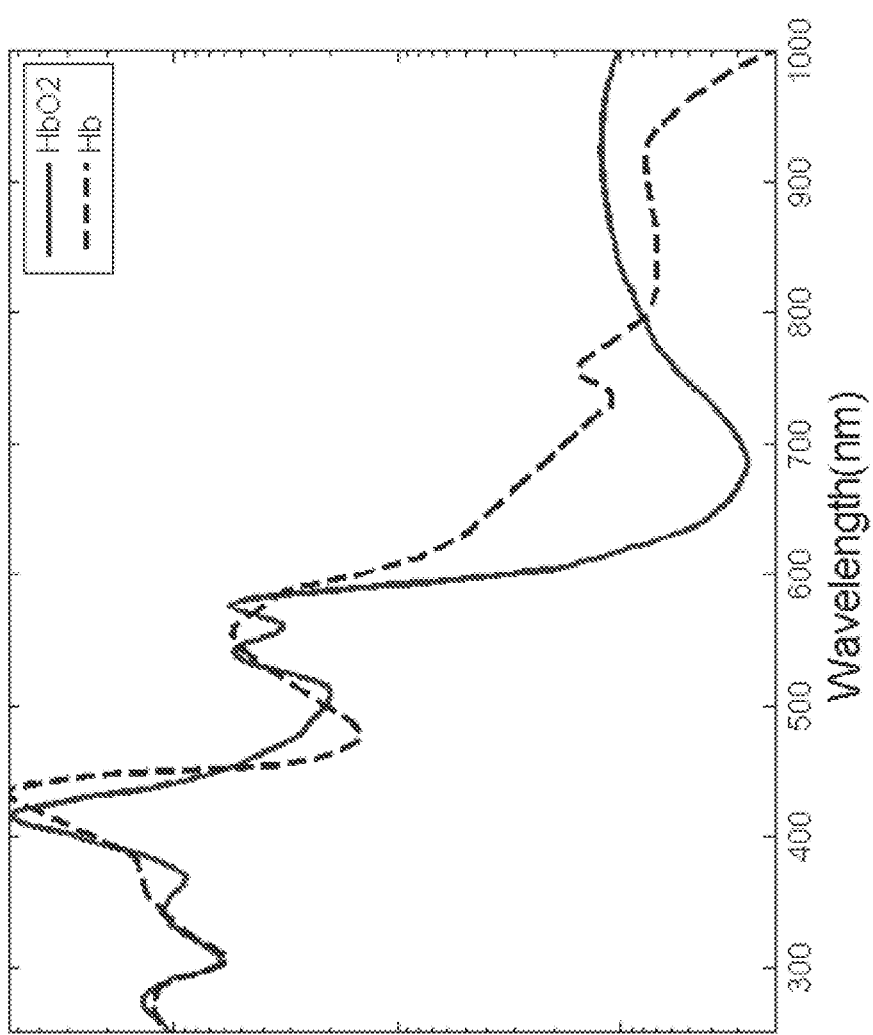
FIG. 8 shows the optical absorption spectra of oxygenated hemoglobin (HbO2) and deoxygenated hemoglobin (Hb) in the ultraviolet, visible, and near infrared region, as provided by Bme591wikiproject at the English language Wikipedia, CC BY-SA 3.0, https://commons.wikimedia.org/w/index.php?curid=3447869.

Reference is now made to FIG. 8, which shows the optical absorption spectra of oxygenated hemoglobin (HbO2) and deoxygenated hemoglobin (Hb) in the ultraviolet, visible and near infrared light region, as provided by Bme591wikiproject at the English language Wikipedia, CC BY-SA 3.0, https://commons.wikimedia.org/w/index.php?curid=3447869. As described hereinabove, for some applications, a blood signature is detected by detecting two or more (and, typically, three or more) spectral components that are indicative of a characteristic shape of a light absorption curve of a component of blood. For example, as described hereinabove, a characteristic trough-peak-trough shape at approximately 540 nm (trough), 565 nm (peak) and 575 nm (trough) may be detected. This characteristic shape is an example of a blood signature, the shape being indicative of the presence of blood. Specifically, this shape indicates light absorption by oxyhemoglobin, which is present in erythrocytes in the blood.

The scope of the present invention includes identifying any set of three or more spectral components that have a characteristic relationship with each other in the light absorption spectrum of a component of blood. Typically, the three or more components are within the ultraviolet, visible, and/or near infrared light regions of the spectrum. For example, a set of three or more spectral components that have a characteristic relationship with each other in the light absorption spectrum of deoxyhemoglobin may be detected. With reference to FIG. 8, an example of such a set of three components is the peak-trough-peak shape exhibited at approximately 435 nm (peak), 480 nm (trough), and 555 nm (peak), in the deoxyhemoglobin light absorption spectrum. For some applications, one of the three spectral components that is used to identify blood is approximately 425 nm (e.g., between 420 and 430 nm). For some applications, one of the three spectral components that is used to identify blood is approximately 500 nm (e.g., between 490 nm and 510 nm). (It is noted that the relationship between these components in the light reflected from the bodily emission will be different to that shown in FIG. 8, since FIG. 8 shows the absorption spectra of oxyhemoglobin and deoxyhemoglobin. The reflected or transmitted light spectrum will exhibit a trough-peak-trough shape, where the absorption spectrum exhibits a peak-trough-peak shape, and vice versa. Similarly, the trough-peak-trough pattern in the oxyhemoglobin curve shown in FIG. 4 (which shows the reflected light spectrum) appears as a peak-trough-peak pattern in FIG. 8.) For some applications, a set of three or more spectral components that have a characteristic relationship with each other in the light absorption spectrum of a different component of blood is detected. For example, the component of blood may include a component of the blood that is present in erythrocytes (e.g., met-hemoglobin, carboxyhemoglobin, and/or heme), and/or a non-erythrocytic component (such as, platelets).

As described hereinabove, for some applications, spectral bands that are centered around the spectral components of interest are detected. The widths of the spectral bands are typically greater than 3 nm (e.g., greater than 5 nm, or greater than 8 nm), and/or less than 40 nm (e.g., less than 20 nm, or less than 12 nm), e.g., between 3 and 40 nm, between 5 and 20 nm, or between 8 and 12 nm.

Typically, in order to distinguish the blood component from other components within the bodily emission, a set of at least three spectral components is detected, in accordance with the techniques described hereinabove. However, the scope of the present invention includes detecting two or more spectral components that have a characteristic relationship with one another in the absorption spectrum of a component of blood. Typically, the components are within the ultraviolet, visible, and/or near infrared light regions of the spectrum, e.g., between 400 nm and 600 nm.

Figure 10:
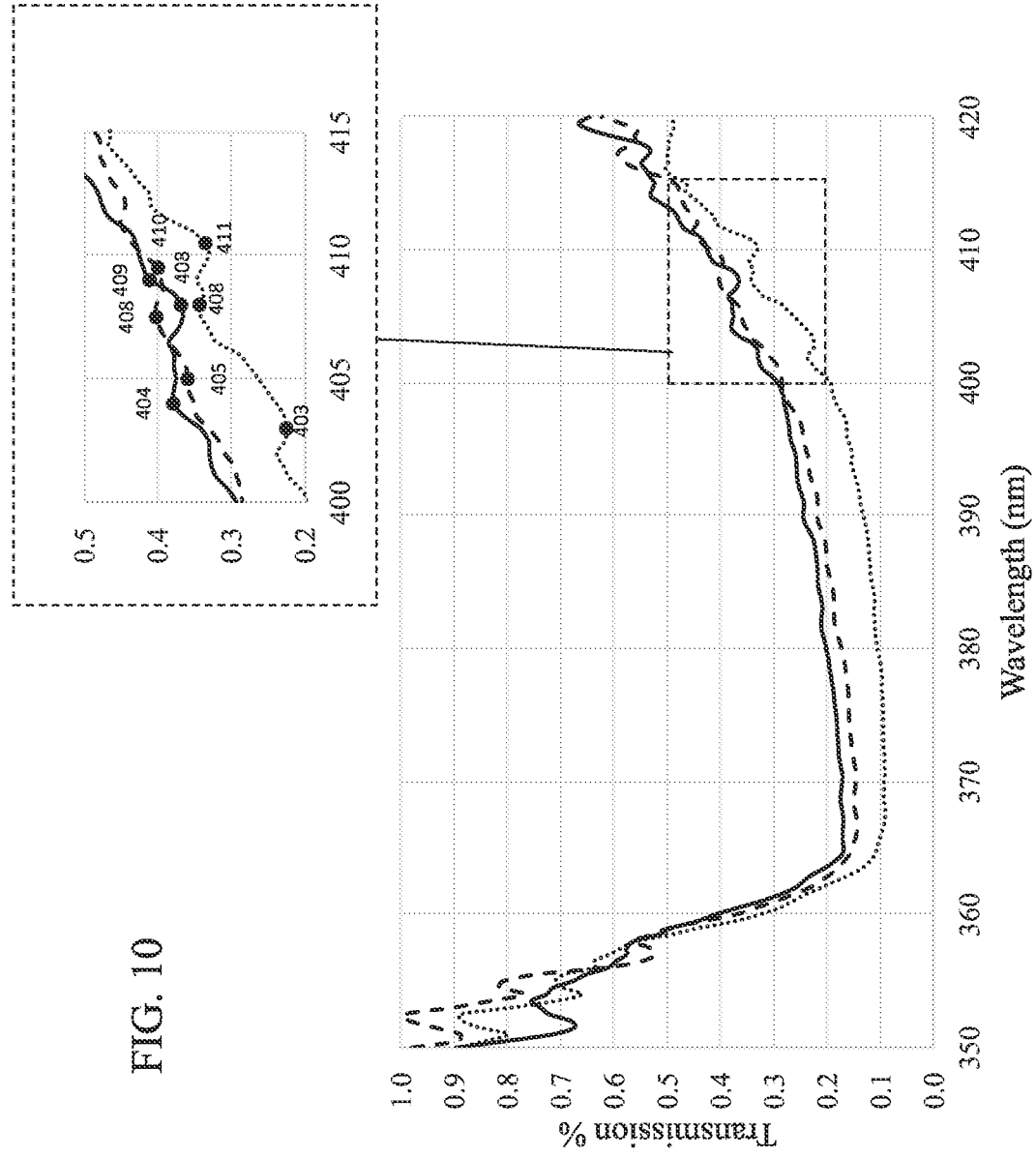
FIG. 10 shows ultraviolet light transmission spectra that were recorded from respective strains of bacteria, in the experiment that was conducted in accordance with some applications of the present invention.

Reference is now made to FIG. 9, which shows infrared light transmission spectra that were recorded from respective strains of bacteria, in an experiment that was conducted in accordance with some applications of the present invention. Reference is also made to FIG. 10, which shows ultraviolet light transmission spectra that were recorded from respective strains of bacteria.

In the experiment, the serotypes O25, O87 of *Escherichia coli* ("*E. coli*") as well as *Lactobacillus plantarum* ("*L. plantarum*") strains were used. All bacteria were grown on Tryptic soy broth (Sigma-Aldrich) medium at 37° C. overnight. The fresh cultures were placed on Petri dishes in equal volumes (5 mL) and subjected to spectral analysis. The experiment was performed over two sessions, using different cultures of bacteria. In the first session, *E. coli* O25 and *L. plantarum* were used, and in the second session, all three of the aforementioned strains were used. As a reference, an additional 5 ml of fresh and clean Tryptic soy broth medium in a Petri dish was used.

Each dish was tested for light transmission using a spectrometer (StellarNet, BLUE-Wave Miniature Spectrometer) attached to an optic fiber (StellarNet, F600 VIS-NIR) and connected to a computer via a USB port. The computer was running SpectraWiz software allowing the reading of photon counts with a wavelength of 200 nm to 1000 nm using the software's scope mode over a set period of time (integration time).

Light sources were used with three different wavelength ranges: white (OPT machine vision PI0803, 400 nm-750 nm), ultraviolet (OPT machine vision PI0803, 360 nm-410 nm) and infrared (860 nm-1000 nm).

The light source and detector were placed on a vertical stand, with the Petri dish placed between the source and the detector, such that the detector would receive photons transmitted from the Petri dish. During the experiment, ambient light was turned off. Initially, the light source was turned on and placed just below the reference dish and optic sensor. Intensity was measured using SpectraWiz software with different integration times in order to find the lowest integration time with the highest peak without saturation (i.e., up to a count of 50,000 photons). Subsequently, the light source was turned off, in order to set the dark spectrum. After doing so each dish was tested for intensity using the light source. For each light source, a new integration time and dark spectrum was set while examining the highest peak of the reference dish. To calculate the transmission of light of the respective strains of bacteria, the intensity of each bacteria strain was divided by the intensity of the reference in order to receive the fraction of light transmitted by the bacteria strain.

FIG. 9 shows the transmission of the respective strains of bacteria that were recorded in the second session, when the infrared light source was used. The top (solid) curve is the transmission spectrum of *E. coli* 25, the middle (dashed) curve is the transmission spectrum of *E. coli* 87, and the bottom (dotted curve) is the transmission spectrum of the *L. plantarum*. It can be observed that there is a difference between the transmission spectra of the respective strains of bacteria. FIG. 10 shows the transmission of the respective strains of bacteria that were recorded in the second session, when the ultraviolet light source was used. Here too, it can be observed that there is a difference between the transmission spectra of the respective strains of bacteria. Similar results were observed when the visible light source was used. With respect to the ultraviolet transmission spectrum shown in FIG. 10, it is hypothesized that at least some of the transmitted light is due to fluorescence of the bacteria.

Therefore, in accordance with some applications of the present invention, light that is transmitted or reflected from a bodily emission (e.g., feces and/or urine) is analyzed in order to identify one or more strains of bacteria, or other microorganisms, that are present in the bodily emission. For some applications, the analysis is performed automatically subsequent to the subject releasing the bodily emission into a toilet bowl, in accordance with the techniques described hereinabove. For some applications, light (e.g., ultraviolet, visible, and/or infrared light is transmitted toward the bodily emission) is transmitted toward the bodily emission, and the light that is transmitted from the bodily emission is detected and analyzed. The transmitted light that is detected may be due to reflectance from microorganisms, and/or due to fluorescence of the microorganisms.

It is noted with respect to the enlarged portions of the spectra shown in FIGS. 9 and 10 that the spectra of the respective strains of bacteria include spectral components that have characteristic relationships with each other. For example, *L. plantarum* has a trough-peak-trough pattern at 854 nm, 857 nm and 859 nm. Similarly, the *E. coli* 87 has a trough-peak-trough pattern at 852 nm, 854 nm and 859 nm. In accordance with these results, for some applications the methods and apparatus described herein for detecting blood inside a bodily emission are used to detect the presence of a given type of microorganism (e.g., a parasitic microorganism, such as a bacterium, a virus, or a fungus) that may be present in the bodily emission. For example, the microorganism may have a characteristic light spectrum (e.g., transmission spectrum, reflectance spectrum, absorption spectrum, and/or fluorescence spectrum). Typically, the microorganism is detected by detecting a set of three or more spectral components that have a characteristic relationship with each other in the light spectrum of the microorganism. For some applications, the microorganism is detected by detecting a set of two or more spectral components that have a characteristic relationship with each other in the light spectrum of the microorganism. Typically, the spectral components are within the ultraviolet, visible and/or near infrared light regions of the spectrum. For some applications, the detected spectral components are due to fluorescence of the microorganism. For some applications, the computer processor determines a level of infection of the subject's gastrointestinal tract based upon the fluorescence signal of the microorganism. For some such applications, in response thereto, the computer processor generates an output indicating that the subject is currently suffering from a condition such as inflammatory bowel disease and/or dysentery, and/or predicting an upcoming event related to such a condition. Alternatively or additionally, the computer processor may generate an output recommending that the subject see a healthcare professional.

For some applications of the present invention, the apparatus and methods described herein are used to detect white blood cells within a bodily emission (such as feces or urine), and/or to classify the white blood cells, e.g., by distinguishing between leukocytes monocytes, neutrophils and/or eosinophils. For example, the computer processor may detect a presence of white blood cells, and/or an amount (e.g., a concentration, a count, and/or a volume) of white blood cells. For some such applications, white blood cells are made to auto-fluoresce by exciting the white blood cells with light that is transmitted from one of the light sources (e.g. using an excitation signal of 250-370 nm, 250-265 nm, and/or 366-436 nm), e.g., in accordance with techniques described in "Natural fluorescence of white blood cells: spectroscopic and imaging study," by Monici et al. (Journal of Photochemistry and Photobiology B:Biology 30 (1995) 29-37). Typically, the presence and/or classification of white blood cells is identified by the computer processor detecting a characteristic signature in the auto-fluorescence signal (e.g., a signature that includes three or more spectral components that have characteristic relationships with each other), in accordance with the techniques described herein. For some applications, the computer processor determines a level of infection of the subject's gastrointestinal tract based upon the auto-fluorescence signal of the white blood cells. For some such applications, in response thereto, the computer processor generates an output indicating that the subject is currently suffering from a condition such as inflammatory bowel disease and/or dysentery, and/or predicting an upcoming event related to such a condition.

Alternatively or additionally, the computer processor may generate an output recommending that the subject see a healthcare professional.

For some applications, the apparatus and methods described herein are used, mutatis mutandis, to detect bodily secretions such as bile, iron, vitamins (such as vitamin A, vitamin B, and/or vitamin D), and/or hormones (such as cortisol, and/or human chorionic gonadotropin). Typically, the bodily secretion is detected by the computer processor detecting a set of three or more spectral components that have a characteristic relationship with each other in the light spectrum (e.g., transmission spectrum, reflectance spectrum, absorption spectrum, and/or fluorescence spectrum) of the bodily secretion, e.g., using the techniques described hereinabove. For some applications, the bodily secretion is detected by the computer processor detecting a set of two or more spectral components that have a characteristic relationship with each other in the light spectrum of the bodily secretion. Typically, the spectral components are within the ultraviolet, visible and/or near infrared light regions of the spectrum. For some applications, the detected spectral components are due to fluorescence of the bodily secretion. For some applications, the apparatus and methods described herein are used to detect the amount and/or concentration of a vitamin that is present in a bodily emission (e.g., urine or feces). For some applications, in response thereto, the apparatus and methods described herein are used to detect overuse of the vitamin by the subject.

For some applications, the apparatus and methods described herein are used, mutatis mutandis, to detect color and/or texture of a subject's feces, and/or to detect color and/or textural changes of the subject's feces over time. For some applications, the presence or concentration of any one of the above-described bodily secretions is detected by the computer processor detecting the color and/or texture of the subject's feces, and/or by detecting color and/or textural changes of the subject's feces over time.

Physiological conditions (such as stress, exertion, pregnancy, etc.), as well as certain pathologies (such as celiac disease, diabetes, mental disorders, hypolactasia, hepatitis, hepatobiliary disease, inflammatory bowel disease, malabsorption syndrome, allergies, inflammation, autoimmune syndromes, etc.) impact the color and/or texture of feces. Therefore, for some applications, at least partially in response to the detected color and/or texture of a subject's feces, and/or the detected color and/or textural changes of the subject's feces over time, the computer processor identifies that the subject is undergoing one or more physiological conditions (such as stress, exertion, pregnancy, etc.). For some applications, at least partially in response to the detected color and/or texture of a subject's feces, and/or the detected color and/or textural changes of the subject's feces over time, the computer processor identifies that the subject is suffering from one or more pathologies (such as celiac disease, diabetes, a mental disorder, hypolactasia, hepatitis, hepatobiliary disease, inflammatory bowel disease, malabsorption syndrome, allergies, inflammation, autoimmune syndromes, etc.). For some applications, at least partially in response to the detected color and/or texture of a subject's feces, and/or the detected color and/or textural changes of the subject's feces over time, the computer processor generates an alert indicating that a subject suffering from inflammatory bowel disease may undergo an episode.

Figure 11:
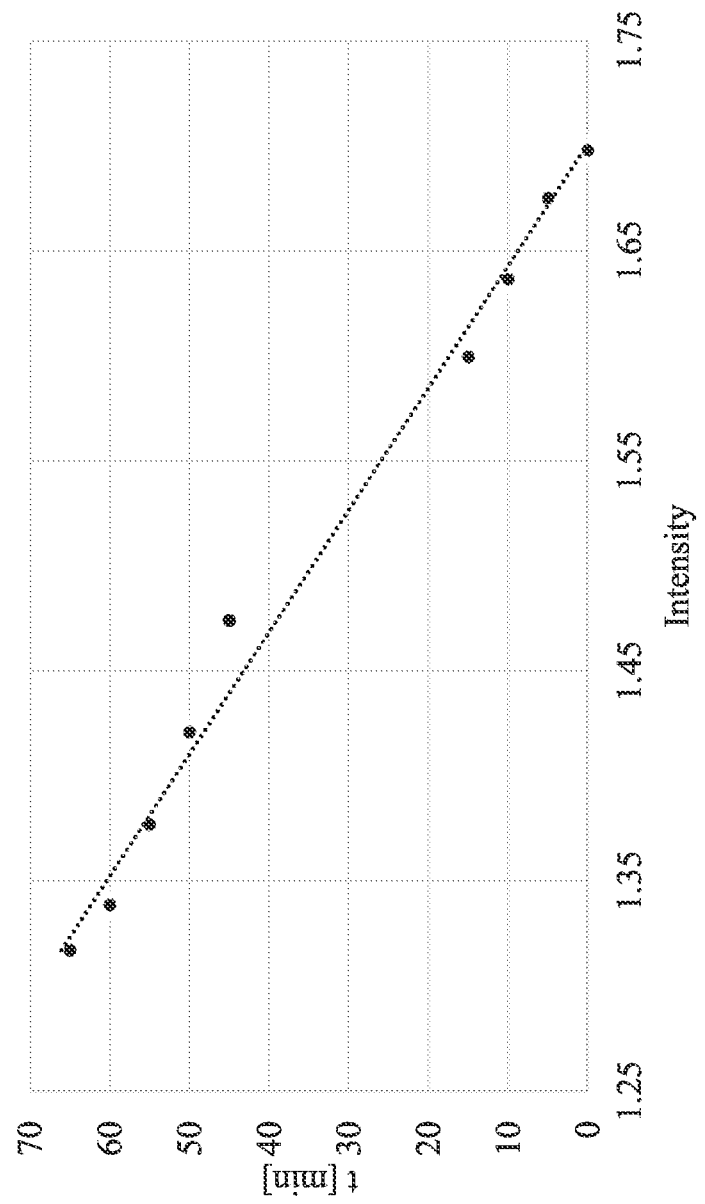
FIG. 11 is a graph showing a relationship between the transmission of light at 800 nm by blood, and the age of the blood in minutes, as measured by the inventors of the present application, and as used, in accordance with some applications of the present invention.

Reference is now made to FIG. 11, which is a graph showing a relationship between the transmission of light at 800 nm by blood, and the time period over which the blood aged in anaerobic conditions in minutes, as measured by the inventors of the present application, and as used, in accordance with some applications of the present invention. A 0.5 ml blood sample was taken from a healthy adult under the age of 45. The sample was then diluted with a phosphate buffered saline ("PBS") solution that was enriched with carbon dioxide, at a ratio of one-part blood to 10-parts carbon dioxide enriched PBS solution. The sample was then placed in a Tecan Infinite® 200 PRO plate reader in 200 nm-1000 nm transmission spectrometry mode and tested for transmission changes over time, for a total of 3 hours 25 minutes.

Figure 12:
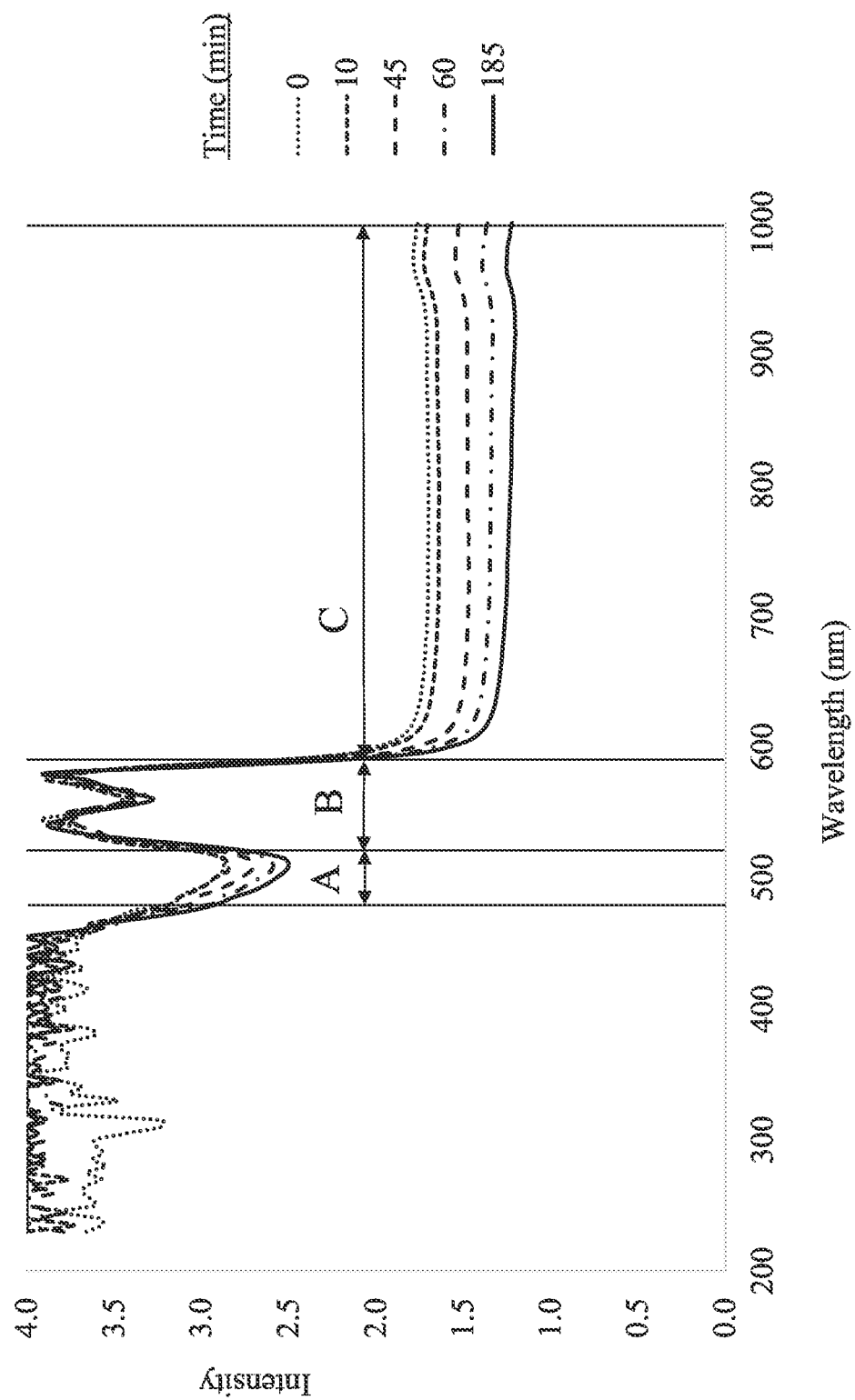
FIG. 12 is shows the optical transmission spectra of blood that has aged by respective time durations in anaerobic conditions, as measured by the inventors of the present application, and as used, in accordance with some applications of the present invention.

FIG. 11 shows the variation between the transmission at 800 nm with the age of the blood sample. It may be observed that there is a linear relationship between the transmission intensity and the age of the blood, with the transmission intensity decreasing as a function of the time period over which the blood has aged in anaerobic conditions Reference is also made to FIG. 12, which shows the optical transmission spectra of blood that was aged over respective time periods in anaerobic conditions, as measured in the above-described experiment, and as used, in accordance with some applications of the present invention. As described with reference to FIG. 11, at 800 nm for example, there is a decrease in the transmission intensity as the blood ages. Similarly, with reference to FIG. 12, at other wavelengths within spectral region C (i.e., between approximately 590 nm and 1000 nm), and at wavelengths within spectral region A (i.e., between approximately 480 nm and 520 nm) there is a decrease in the transmission intensity as the blood ages. By contrast, as shown in FIG. 12, within the spectral region B (i.e., between approximately 520 nm and 590 nm), blood has generally similar transmission intensity, regardless of the time period over which the blood has aged in anaerobic conditions.

Figure 13:
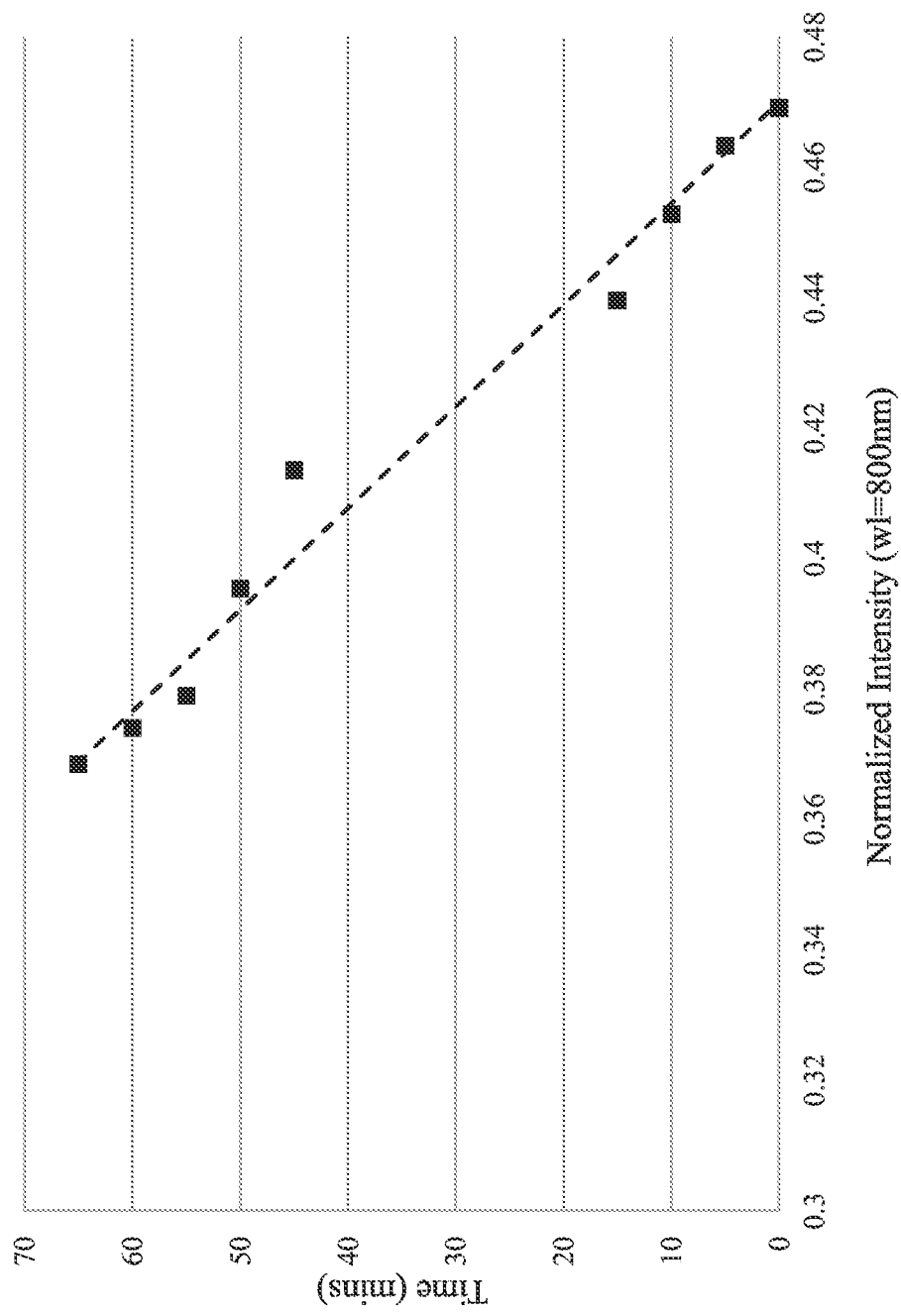
FIG. 13 is a graph showing a relationship between (a) the transmission of light at 800 nm by blood, the transmission having been normalized by light transmission at other wavelengths, and (b) the age of the blood in minutes, as measured by the inventors of the present application, and as used, in accordance with some applications of the present invention.

Reference is now made to FIG. 13, which is a graph showing a relationship between (a) the transmission of light at 800 nm by blood, the transmission having been normalized by light transmission at other wavelengths, and (b) the age of the blood in minutes, as measured by the inventors of the present application, and as used, in accordance with some applications of the present invention. As described with reference to FIG. 12, within certain spectral regions (e.g., regions A and C in FIG. 12), the transmission of blood varies as the time periods over which the blood has aged in anaerobic conditions increases, while in other spectral regions (e.g., region B in FIG. 12), blood has generally similar transmission intensity, regardless of the time period over which the blood has aged in anaerobic conditions. If the transmission at which wavelengths at which the transmission varies with the age of the blood is normalized with respect to the transmission at wavelengths at which the transmission remains constant, then it follows that this should provide a good indication of the age of the blood, the indication being independent of the absolute transmission that is detected. Therefore, using the results measured in the above-described experiment, the transmission detected at 800 nm for each of the ages of the blood was normalized by calculating the ratio of the transmission at 800 nm to the transmission at (a) 535-545 nm, (b) 555-565 nm, and (c) 575-585. The mean of these ratios was then calculated to provide a normalized measure of transmission detected at 800 nm for each of the ages of the blood. FIG. 13 shows a plot of the normalized transmission intensity at 800 nm against the time over which the blood was aged in anaerobic conditions. It may be observed that there is a linear relationship between the normalized intensity at 800 nm and the time over which the blood aged in anaerobic conditions, with the transmission intensity decreasing as a function of the time period over which the blood has aged in anaerobic conditions. The above-described results indicate that the transmission intensity of blood that is within a bodily emission could be used to provide an indication of how long the blood has aged in anaerobic conditions, and thereby provide an indication of a source of the blood from within the gastrointestinal tract. Moreover, if the transmission intensity at certain wavelengths (e.g., those within regions A and C of FIG. 12) are normalized with respect to the transmission intensity at other wavelengths (e.g., those within region B of FIG. 12), this could be used to provide an indication of how long the blood has aged in anaerobic conditions that is independent of absolute transmission intensity.

In accordance with the above-described results, for some applications of the present invention, apparatus 20 (shown in FIG. 1) is used to detect blood within feces, for example, using the techniques described hereinabove. For some applications, the apparatus is additionally configured to determine a source of the blood from within the subject's gastrointestinal tract (e.g., whether the blood is from an upper gastrointestinal tract bleeding site, which might indicate that the subject has polyps, or from a lower bleeding site, which may be due to an anal injury, for example). In response thereto, the apparatus typically generates an output. For example, the apparatus may generate an alert indicating that the subject should visit a healthcare professional in response to detecting blood from an upper gastrointestinal tract bleeding site.

Typically, as blood within feces passes through the gastrointestinal tract it is within an anaerobic environment. Therefore, for some applications, the results demonstrated in FIGS. 11-13 are implemented in determining the source of blood within feces. Typically, computer processor 44 normalizes (a) the intensities of one or more spectral components that are within a range of 480-520 nm (corresponding to region A of FIG. 12) and/or 590-1000 nm (corresponding to region C of FIG. 12) with respect to (b) the intensities of one or more spectral components that are within a range of 520-590 nm (corresponding to region B of FIG. 12). Typically, the computer processor determines the age of the blood based upon the normalized intensities. For some applications, the computer processor determines the source of blood that is present in the feces from within the gastrointestinal tract, and in response thereto, generates an output. For example, the computer processor may generate an indication of a presence of blood within the feces as well as an indication of a likely source of the blood, an indication of a predicted upcoming episode (e.g., an inflammatory bowel disease episode), and/or an indication that the subject should see a healthcare professional.

For example, a ratio between (a) the intensity of a spectral component that has a wavelength of between approximately 480 nm and 520 nm (corresponding to region A of FIG. 12) and (b) the intensity of a spectral component that has a wavelength of between approximately 520 nm and 590 nm (corresponding to region B of FIG. 12) may be determined. Alternatively or additionally, a ratio between (a) the intensity of a spectral component that has a wavelength of between approximately 590 nm and 1000 nm (corresponding to region C of FIG. 12) and (b) the intensity of a spectral component that has a wavelength of between approximately 520 nm and 590 nm (corresponding to region B of FIG. 12) may be determined. For some applications, an average (e.g., a mean, or a weighted mean) of two or more such ratios is determined. For some applications, three or more spectral components are detected, and a relationship between their intensities is determined in order to determine the source of blood within feces. For example, a first one of the components may have a wavelength of between 480 nm and 520 nm (corresponding to region A of FIG. 12), the second component may have a wavelength of between approximately 520 nm and 590 nm (corresponding to region B of FIG. 12), and the third component may have a wavelength of between approximately 590 nm and 1000 nm (corresponding to region C of FIG. 12).

For some applications, as an alternative to, or in addition to, analyzing the spectral profile of the blood within the feces, apparatus 20 analyzes the spatial distribution of the blood within the feces, in order to determine the source of the blood from within the gastrointestinal tract. For example, the computer processor may analyze the extent to which the blood is spread throughout the feces, and/or the location of the blood within the feces. Typically, in response to detecting that the blood is evenly spread, the system determines that the source of the blood is from the upper colorectal tract, within which feces are relatively fluidic, such that the blood can spread evenly, and within which peristalsis mixes the feces and the blood. Further typically, in response to detecting the blood is disposed within isolated volumes within the feces, the system determines that the source of the blood is from a downstream bleeding site within the colorectal tract, where the feces are typically more solid, such that the blood cannot spread evenly through the feces as a result of peristaltic mixing, which results in the blood being spread more irregularly through the feces. Still further typically, if the blood is smeared onto the surface of the feces or diffused in the water of the toilet bowl, the system determines that source of the blood is from adjacent to and/or at the rectum.

In accordance with the description of FIG. 1, typically, in order to perform the above-described steps, the subject is not required to physically touch the feces. Furthermore, the subject is typically only required to touch any portion of the dedicated sensing apparatus periodically, for example, in order to install the device, or to change or recharge the device batteries. (It is noted that the subject may handle the user interface device, but this is typically a device (such as a phone) that subject handles even when not using the sensing apparatus.) Further typically, performance of the above-described steps does not require adding anything to the toilet bowl subsequent to the subject emitting a bodily emission into the toilet bowl, in order to facilitate the spectral analysis of the emission, a determination that the emission contains blood, and/or determination of a source of the blood. For some applications, the subject is not required to perform any action after installation of the apparatus in the toilet bowl. The testing is automatic and handled by the apparatus, and monitoring of the subject's emissions is seamless to the subject and does not require compliance by the subject, so long as no abnormality is detected.

Figure 14:
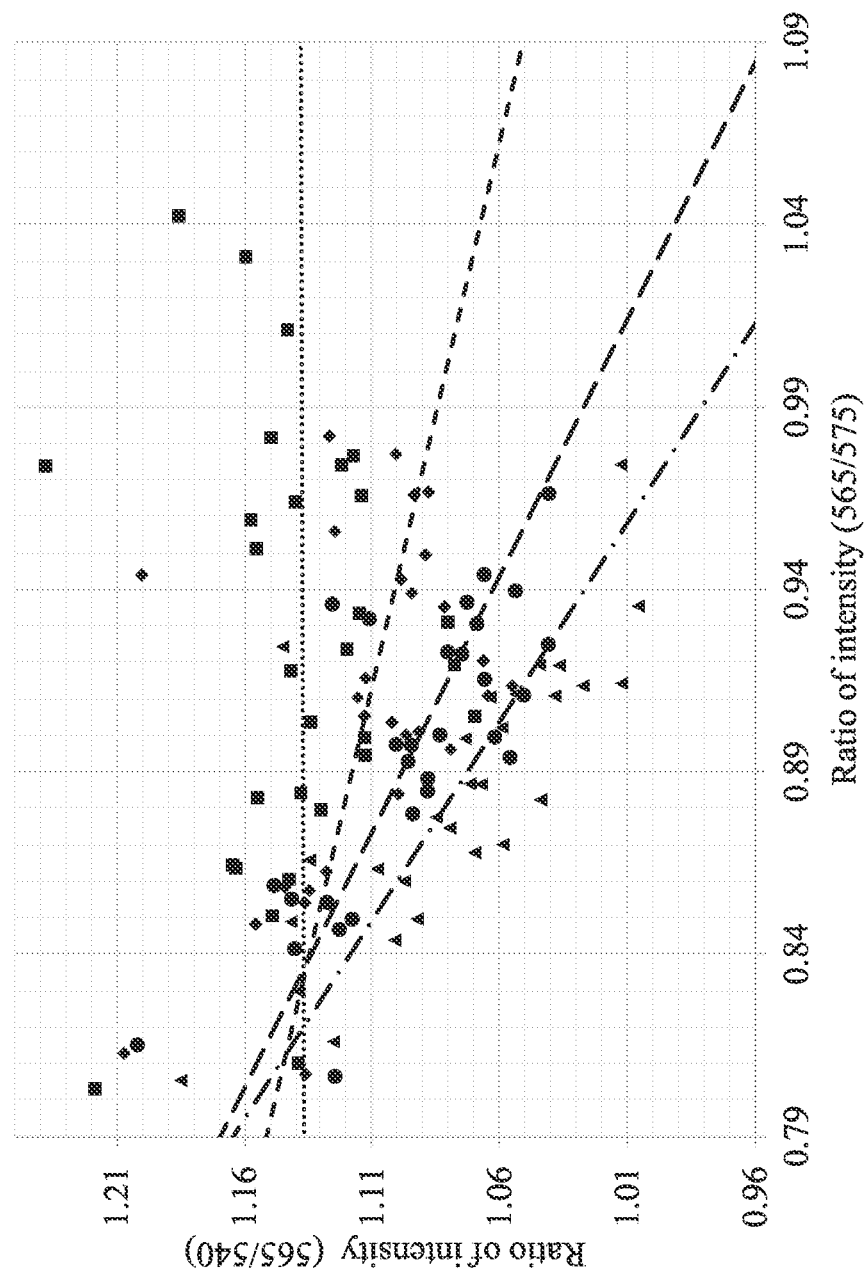
FIG. 14 is a scatter plot on which ratios of light intensities that were reflected from stool samples having respective volumes of blood mixed therewith are plotted, as measured by the inventors of the present application, and as used, in accordance with some applications of the present invention.

Reference is now made to FIG. 14, which is a scatter plot on which ratios of light intensities that were reflected from stool samples having respective volumes of blood mixed therewith are plotted, as measured by the inventors of the present application, and as used, in accordance with some applications of the present invention.

As described hereinabove, for some applications of the present invention, two or more spectral bands are detected that are centered around approximately 540 nm, 565 nm, and 575 nm. For some applications, the detected spectral components are analyzed by calculating ratios of the intensities of respective components with respect to one another. For example, the ratio of the intensity of a 10 nm band centered around 565 nm, to the intensity of a 10 nm band centered around 575 nm (I(565)/I(575)) may be calculated, and/or the ratio of the intensity of a 10 nm band centered around 565 nm, to the intensity of a 10 nm band centered around 540 nm (I(565)/I(540)) may be calculated. In response to the spectral analysis, the computer processor detects blood within a bodily emission and generates an output, for example, on user interface device 32.

An experiment was conducted in which 30 samples of 100 g of feces were mixed with 4 different doses of blood: 0 microliters, 125 microliters, 250 microliters, and 500 microliters. For each of the samples, the aforementioned intensity ratios (I(565)/I(575) and I(565)/I(540)) were measured. FIG. 14 shows a scatter plot of the intensity ratios as recorded for each of the samples. The results for the samples with 0 microliters of blood are indicated with triangular markers and the linear trendline for such samples is indicated by a dashed and dotted line. The results for the samples with 125 microliters of blood are indicated with circular markers and the linear trendline for such samples is indicated by the dashed line with the large dashes. The results for the samples with 250 microliters of blood are indicated with diamond markers and the linear trendline for such samples is indicated by the dashed line with the small dashes. The results for the samples with 500 microliters of blood are indicated with square markers and the linear trendline for such samples is indicated by the dotted line. The results shown in FIG. 14 indicate that intensity ratios as described herein can be indicative not only of the presence of blood in a bodily emission (such as urine or feces), but also of the amount (e.g., concentration, or volume) of the blood in the emission.

Therefore, in accordance with some applications of the present invention, spectral bands that are centered around a wavelength that is in the range of 530 nm to 785 nm (e.g., between 530 nm and 600 nm) are detected within a bodily emission (such as urine or feces) that is disposed within a toilet bowl, in accordance with the techniques described hereinabove. Typically, two or more spectral bands are detected that are centered around approximately 540 nm, 565 nm, and 575 nm. The widths of the spectral bands are typically greater than 3 nm (e.g., greater than 5 nm, or greater than 8 nm), and/or less than 40 nm (e.g., less than 20 nm, or less than 12 nm), e.g., between 3 and 40 nm, between 5 and 20 nm, or between 8 and 12 nm. For some applications, one or more ratios of the intensities of the aforementioned spectral bands with respect to one another are determined by the computer processor. For example, the ratio of the intensity of the spectral band that is centered around approximately 565 nm to that of the band centered around approximately 575 nm (or vice versa) may be determined, and/or the ratio of the intensity of the spectral band that is centered around approximately 565 nm to that of the band centered around approximately 540 nm (or vice versa) may be determined. For some applications, a different relationship between the intensities of the aforementioned spectral bands with respect to one another is determined by the computer processor. For some applications, a relationship between a parameter of the respective spectral bands other than intensity is determined. For some applications, other spectral bands that are indicative of blood are measured. For example, a spectral band centered around approximately 425 nm (e.g., between 420 and 430 nm) and/or a spectral band centered around approximately 500 nm (e.g., between 490 and 510 nm) may be detected and used in a generally similar manner.

In response to the above-described measurements, the computer processor determines (a) that there is a presence of blood within the bodily emission, and (b) estimates the amount (e.g., concentration or volume) of the blood within the bodily emission. Typically, the computer processor generates an output in response to the estimated concentration (for example, on user interface device 32). For example, the computer processor may generate an output recommending that the subject should see a healthcare professional, or an output indicating a predicted upcoming inflammatory bowel disease episode.

Applications of the invention described herein can take the form of a computer program product accessible from a computer-usable or computer-readable medium (e.g., a non-transitory computer-readable medium) providing program code for use by or in connection with a computer or any instruction execution system, such as computer processor 44, or a computer processor of user interface device 32. For the purpose of this description, a computer-usable or computer readable medium can be any apparatus that can comprise, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Typically, the computer-usable or computer readable medium is a non-transitory computer-usable or computer readable medium.

Examples of a computer-readable medium include a semiconductor or solid-state memory, magnetic tape, a removable computer diskette, a random-access memory (RAM), a read-only memory (ROM), a rigid magnetic disk and an optical disk. Current examples of optical disks include compact disk-read only memory (CD-ROM), compact disk-read/write (CD-R/W) and DVD. For some applications, cloud storage is used.

A data processing system suitable for storing and/or executing program code will include at least one processor (e.g., computer processor 44, or a computer processor of user interface device 32) coupled directly or indirectly to memory elements (e.g., memory 46, or a memory of user interface device 32) through a system bus. The memory elements can include local memory employed during actual execution of the program code, bulk storage, and cache memories which provide temporary storage of at least some program code in order to reduce the number of times code must be retrieved from bulk storage during execution. The system can read the inventive instructions on the program storage devices and follow these instructions to execute the methodology of the embodiments of the invention.

Network adapters may be coupled to the processor to enable the processor to become coupled to other processors or remote printers or storage devices through intervening private or public networks. Modems, cable modem and Ethernet cards are just a few of the currently available types of network adapters.

Computer program code for carrying out operations of the present invention may be written in any combination of one or more programming languages, including an object-oriented programming language such as Java, Smalltalk, C++ or the like and conventional procedural programming languages, such as the C programming language or similar programming languages.

It will be understood that blocks of the flowchart shown in FIG. 7 and combinations of blocks in the flowchart, can be implemented by computer program instructions. These computer program instructions may be provided to a processor of a general purpose computer, special purpose computer, or other programmable data processing apparatus to produce a machine, such that the instructions, which execute via the processor of the computer (e.g., computer processor 44, or a computer processor of user interface device 32) or other programmable data processing apparatus, create means for implementing the functions/acts specified in the flowchart and/or algorithms described in the present application. These computer program instructions may also be stored in a computer-readable medium (e.g., a non-transitory computer-readable medium) that can direct a computer or other programmable data processing apparatus to function in a particular manner, such that the instructions stored in the computer-readable medium produce an article of manufacture including instruction means which implement the function/act specified in the flowchart blocks and algorithms. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide processes for implementing the functions/acts specified in the flowchart and/or algorithms described in the present application.

Computer processor 44 and the other computer processors described herein are typically hardware devices programmed with computer program instructions to produce a special purpose computer. For example, when programmed to perform the algorithms described with reference to FIGS. 7, the computer processor typically acts as a special purpose bodily-emission-analysis computer processor. Typically, the operations described herein that are performed by computer processors transform the physical state of a memory, which is a real physical article, to have a different magnetic polarity, electrical charge, or the like depending on the technology of the memory that is used.

There is provided, in accordance with some applications of the present invention, the following inventive concepts:

Inventive concept 1. A method for use with a bodily emission of a subject that is disposed within a toilet bowl, the method comprising:
  while the bodily emission is disposed within the toilet bowl, receiving light from the toilet bowl using one or more light sensors;
  using a computer processor:
    detecting a set of three or more spectral components that have a characteristic relationship with each other in a light absorption spectrum of a component of blood, by analyzing the received light;
    in response thereto, determining that there is a presence of blood within the bodily emission; and
    generating an output on an output device, at least partially in response thereto.

Inventive concept 2. The method according to inventive concept 1, wherein the bodily emission includes feces, and wherein determining that there is a presence of blood within the bodily emission comprises determining that there is a presence of blood within the feces.

Inventive concept 3. The method according to inventive concept 1, wherein the bodily emission includes urine, and wherein determining that there is a presence of blood within the bodily emission comprises determining that there is a presence of blood within the urine.

Inventive concept 4. The method according to inventive concept 1, wherein detecting the set of three or more spectral components that have the characteristic relationship with each other in the light absorption spectrum of the component of blood comprises detecting a set of three or more spectral components that have a characteristic relationship with each other in a light absorption spectrum of a component of blood selected from the group consisting of: oxyhemoglobin, deoxyhemoglobin, methemoglobin, carboxyhemoglobin, heme, and platelets.

Inventive concept 5. Apparatus for use with a bodily emission of a subject that is disposed within a toilet bowl, and an output device, the apparatus comprising:
  one or more light sensors that are configured to receive light from the toilet bowl, while the bodily emission is disposed within the toilet bowl; and
  a computer processor configured to:
    detect a set of three or more spectral components that have a characteristic relationship with each other in a light absorption spectrum of a component of blood, by analyzing the received light;
    in response thereto, determine that there is a presence of blood within the bodily emission; and
    generate an output on the output device, at least partially in response thereto.

Inventive concept 6. The apparatus according to inventive concept 5, wherein the bodily emission includes feces, and wherein the computer processor is configured to determine that there is a presence of blood within the bodily emission by determining that there is a presence of blood within the feces.

Inventive concept 7. The apparatus according to inventive concept 5, wherein the bodily emission includes urine, and wherein the computer processor is configured to determine that there is a presence of blood within the bodily emission by determining that there is a presence of blood within the urine.

Inventive concept 8. The apparatus according to inventive concept 5, wherein the computer processor is configured to detect the set of three or more spectral components that have the characteristic relationship with each other in the light absorption spectrum of the component of blood by detecting a set of three or more spectral components that have a characteristic relationship with each other in a light absorption spectrum of a component of blood selected from the group consisting of: oxyhemoglobin, deoxyhemoglobin, methemoglobin, carboxyhemoglobin, heme, and platelets.

Inventive concept 9. Apparatus for use with a bodily emission of a subject that is disposed within a toilet bowl, and an output device, the apparatus comprising:
  one or more light sensors that are configured to receive light from the toilet bowl, while the bodily emission is disposed within the toilet bowl; and
  a computer processor configured to:
    detect a set of three or more spectral components that have a characteristic relationship with each other in a light absorption spectrum of a component of blood, by analyzing the received light;
    in response thereto, estimate an amount of blood within the bodily emission; and
    generate an output on the output device, at least partially in response thereto.

Inventive concept 10. The apparatus according to inventive concept 9, wherein the computer processor is configured to estimate the amount of blood within the bodily emission by estimating a concentration of blood within the bodily emission.

Inventive concept 11. The apparatus according to inventive concept 9, wherein the computer processor is configured to estimate the amount of blood within the bodily emission by estimating a volume of blood within the bodily emission.

Inventive concept 12. The apparatus according to inventive concept 9, wherein the bodily emission includes feces, and wherein the computer processor is configured to estimate the amount of blood within the bodily emission by estimating an amount of blood within the feces.

Inventive concept 13. The apparatus according to inventive concept 9, wherein the bodily emission includes urine, and wherein the computer processor is configured to estimate the amount of blood within the bodily emission by estimating an amount of blood within the urine.

Inventive concept 14. The apparatus according to inventive concept 9, wherein the computer processor is configured to detect the set of three or more spectral components that have the characteristic relationship with each other in the light absorption spectrum of the component of blood by detecting a set of three or more spectral components that have a characteristic relationship with each other in a light absorption spectrum of a component of blood selected from the group consisting of: oxyhemoglobin, deoxyhemoglobin, methemoglobin, carboxyhemoglobin, heme, and platelets.

Inventive concept 15. A method for use with a bodily emission of a subject that is disposed within a toilet bowl, the method comprising:
  while the bodily emission is disposed within the toilet bowl, receiving light from the toilet bowl using one or more light sensors;
  using a computer processor:
  detecting a set of three or more spectral components that have a characteristic relationship with each other in a light absorption spectrum of a component of blood, by analyzing the received light;
  in response thereto, estimating an amount of blood within the bodily emission; and
  generating an output on an output device, at least partially in response thereto.

Inventive concept 16. The method according to inventive concept 15, wherein estimating the amount of blood within the bodily emission comprises estimating a concentration of blood within the bodily emission.

Inventive concept 17. The method according to inventive concept 15, wherein estimating the amount of blood within the bodily emission comprises estimating a volume of blood within the bodily emission.

Inventive concept 18. The method according to inventive concept 15, wherein the bodily emission includes feces, and wherein estimating the amount of blood within the bodily emission comprises estimating an amount of blood within the feces.

Inventive concept 19. The method according to inventive concept 15, wherein the bodily emission includes urine, and wherein estimating the amount of blood within the bodily emission comprises estimating an amount of blood within the urine.

Inventive concept 20. The method according to inventive concept 15, wherein detecting the set of three or more spectral components that have the characteristic relationship with each other in the light absorption spectrum of the component of blood comprises detecting a set of three or more spectral components that have a characteristic relationship with each other in a light absorption spectrum of a component of blood selected from the group consisting of: oxyhemoglobin, deoxyhemoglobin, methemoglobin, carboxyhemoglobin, heme, and platelets.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. An apparatus for use with feces of a subject that are disposed within a toilet bowl, and an output device, the apparatus comprising:
  one or more light sensors that are configured to receive light from the toilet bowl, while the feces are disposed within the toilet bowl; and
  a computer processor configured to:
    detect a set of three or more spectral components that have a characteristic relationship with each other in a light spectrum of bile, by analyzing the received light;
    detect a presence of bile within the feces, in response to detecting the set of three or more spectral components; and
    generate an output on the output device, at least partially in response thereto.

2. The apparatus according to claim 1, wherein the computer processor is configured to predict an upcoming inflammatory bowel disease episode, at least partially based on detecting the presence of bile within the feces.

3. The apparatus according to claim 1, wherein the computer processor is configured to detect a currently-occurring inflammatory bowel disease episode, at least partially based on detecting the presence of bile within the feces.

4. The apparatus according to claim 1, wherein the computer processor is configured to detect the set of three or more spectral components by detecting a set of three or more spectral components that have a characteristic relationship with each other in a transmission spectrum of bile.

5. The apparatus according to claim 1, wherein the computer processor is configured to detect the set of three or more spectral components by detecting a set of three or more spectral components that have a characteristic relationship with each other in a reflectance spectrum of bile.

6. The apparatus according to claim 1, wherein the computer processor is configured to detect the set of three or more spectral components by detecting a set of three or more spectral components that have a characteristic relationship with each other in an absorption spectrum of bile.

7. The apparatus according to claim 1, wherein the computer processor is configured to detect the set of three or more spectral components by detecting a set of three or more spectral components that have a characteristic relationship with each other in a fluorescence spectrum of bile.

8. The apparatus according to claim 1, wherein the computer processor is further configured to:
  detect a second set of three or more spectral components that have a characteristic relationship with each other in a light spectrum of a microorganism by analyzing the received light; and
  detect a presence of the microorganism within the feces, in response to detecting the second set of three or more spectral components.

9. The apparatus according to claim 1, wherein the computer processor is further configured to:
  detect one or more white blood cell spectral components that are characteristic spectral components at which white blood cells emit fluorescent light microorganism by analyzing the received light; and detect a presence of white blood cells within the feces, in response to detecting the one or more white blood cell spectral components.

10. The apparatus according to claim 1, wherein the computer processor is further configured to:
    detect blood within the feces by analyzing the received light; and
    determine a source of the blood from within a gastrointestinal tract of the subject.

11. A method for use with feces of a subject that are disposed within a toilet bowl, and an output device, the method comprising:
    using one or more light sensors, receiving light from the toilet bowl, while the feces are disposed within the toilet bowl; and
    using a computer processor:
        detecting a set of three or more spectral components that have a characteristic relationship with each other in a light spectrum of bile, by analyzing the received light;
        detecting a presence of bile within the feces, in response to detecting the set of three or more spectral components; and
        generating an output on the output device, at least partially in response thereto.

12. The method according to claim 11, further comprising predicting an upcoming inflammatory bowel disease episode, at least partially based on detecting the presence of bile within the feces.

13. The method according to claim 11, further comprising detecting a currently-occurring inflammatory bowel disease episode, at least partially based on detecting the presence of bile within the feces.

14. The method according to claim 11, wherein detecting the set of three or more spectral components comprises detecting a set of three or more spectral components that have a characteristic relationship with each other in a transmission spectrum of bile.

15. The method according to claim 11, wherein detecting the set of three or more spectral components comprises detecting a set of three or more spectral components that have a characteristic relationship with each other in a reflectance spectrum of bile.

16. The method according to claim 11, wherein detecting the set of three or more spectral components comprises detecting a set of three or more spectral components that have a characteristic relationship with each other in an absorption spectrum of bile.

17. The method according to claim 11, wherein detecting the set of three or more spectral components comprises detecting a set of three or more spectral components that have a characteristic relationship with each other in a fluorescence spectrum of bile.

18. The method according to claim 11, further comprising:
    detecting a second set of three or more spectral components that have a characteristic relationship with each other in a light spectrum of a microorganism by analyzing the received light; and
    detecting a presence of the microorganism within the feces, in response to detecting the second set of three or more spectral components.

19. The method according to claim 11, further comprising:
    detecting one or more white blood cell spectral components that are characteristic spectral components at which white blood cells emit fluorescent light by analyzing the received light; and
    detecting a presence of white blood cells within the feces, in response to detecting the one or more white blood cell spectral components.

20. The method according to claim 11, further comprising:
    detecting blood within the feces by analyzing the received light; and
    determining a source of the blood from within a gastrointestinal tract of the subject.

21. A method for use with feces of a subject that are disposed within a toilet bowl, and an output device, the method comprising:
    using one or more light sensors, receiving light from the toilet bowl, while the feces are disposed within the toilet bowl; and
    using a computer processor:
        detecting a presence of bile within the feces, in response to detecting spectral components within the received light;
        in response thereto, detecting at least one inflammatory bowel disease episode of the subject selected from the group consisting of: a currently-occurring inflammatory bowel disease episode, and a predicted upcoming inflammatory bowel disease episode; and
        generating an output on the output device, at least partially in response thereto.

* * * * *